United States Patent
Ben-Artzi et al.

(10) Patent No.: US 6,190,875 B1
(45) Date of Patent: Feb. 20, 2001

(54) METHOD OF SCREENING FOR POTENTIAL ANTI-METASTATIC AND ANTI-INFLAMMATORY AGENTS USING MAMMALIAN HEPARANASE AS A PROBE

(75) Inventors: Hanna Ben-Artzi, Zion; Maty Ayal-Hershkovitz, Herzliya; Israel Vlodavsky; Iris Pecker, both of Zion; Yoav Peleg; Daphna Miron, both of Rehovot, all of (IL)

(73) Assignees: Insight Strategy & Marketing Ltd.; Hadasit Medical Research & Development Ltd., both of (IL)

( * ) Notice: Under 35 U.S.C. 154(b), the term of this patent shall be extended for 0 days.

(21) Appl. No.: 09/113,168

(22) Filed: Jul. 10, 1998

Related U.S. Application Data

(63) Continuation-in-part of application No. 09/109,386, filed on Jul. 2, 1998, now abandoned, which is a continuation-in-part of application No. 08/922,170, filed on Sep. 2, 1997, now Pat. No. 5,968,822.

(51) Int. Cl.[7] .............................. C12Q 1/34; C12N 9/26
(52) U.S. Cl. ............................................ 435/18; 435/201
(58) Field of Search ....................................... 435/18, 201

(56) References Cited

U.S. PATENT DOCUMENTS

| | | | |
|---|---|---|---|
| 4,859,581 | * | 8/1989 | Nicholson et al. ........................ 435/4 |
| 4,882,318 | * | 11/1989 | Vlodavsky et al. .................... 514/56 |
| 5,129,877 | * | 7/1992 | Gallo et al. .............................. 600/12 |
| 5,206,223 | * | 4/1993 | Vlodavsky et al. .................... 514/56 |
| 5,332,812 | * | 7/1994 | Nicholson et al. ..................... 536/21 |
| 5,362,641 | * | 11/1994 | Fuks et al. ............................. 435/209 |
| 5,399,351 | * | 3/1995 | Leshchiner et al. ................. 424/422 |
| 5,550,116 | * | 8/1996 | Lormeau et al. ....................... 514/56 |
| 5,667,501 | * | 9/1997 | Fowler et al. ......................... 604/304 |
| 5,739,115 | * | 4/1998 | Fugedi et al. ........................... 514/24 |

OTHER PUBLICATIONS

Nakajima et al., "A Solid–Phase Substarte of Heparanse: Its Application to Assay of Human Melanoma fpr Heparan Sulfate Degradative Activity", Analytical Biochemistry, 157: 162–171, 1986.

Oosta et al., "Purification and Properties of Human Platalet Heparitanase", J. Biol. Chem, 257(19): 11249–11255, 1982.

Sewell et al., "Human Mononuclear Cells Contain an Endoglycosidase Specific for Heparan Sulfate Glycosaminoglycan Demonstrable with the Use of a Specific Solid–Phase Metabolically Radiolabelled Subtrate", Biochem J., 264: 777–783, 1989.

Freeman et al., "A Rapid Quantitative Assay for the Detection of Mammalian Heparanse Activity", Biochem J., 325: 229–237, 1997.

Mullings et al., "New Reducing Sugar Assay for the Study of Cellulases", Enzyme Microb. Technol., 6:491–496, 1984.

Taylor et al., "A colorimetric Method for the Quantitation of Uronic Acids and a Specific Assay for Galacturonic Acids", Analytical Biochemistry, 201: 190–196, 1992.

Linhardt, R.J., lary Electrophoresis of Oligosaccharides, Method in Enzmology, 230: 265–280, 1994.

Basu et al., "Analysis of Glycospinggolipids by Fluorophore–Assisted Carbohydrate Electrophoresis Using Ceramide Glycanase from Mercenaria mercenaria", Analytical Biochemistry, 222:270–274, 1994.

Jackson, P., "The Use of Polyacrylamide–gel Electrophoresos for the High–Resolution of Seperation of Reducing Saccharides Labelled with the Fluorophore 8–aminonaphthalene–1,3,6–trisulphonic Acid", Biochem J., 270: 705–713, 1990.

Coquet et al., "Application of a Post–Column Fluorigenic Reaction in Liquid Chromotagraphy for the Determination of Glucose and Fructose in Biological Matrices", Analytica Chemica Acta, 252: 173–179, 1991.

Regan et al., "Mimicry of Biological Macromolecules by Polyaromatic Anionic Compounds", J. Bioactive and Compatible Polymers, 8: 317–337, 1993.

Benezara et al., "Antiproliferative Activity to Vascular Smooth Muscle Cells and Receptor Binding of Heparain–Mimicking Polyaromatic Compounds", Arteriosclerosis and Thrombosis, 14(12): 1992–1999, 1993.

Katz et al., "Antiproliferative Activity to Glomerural Mesangial Cells and Receptor Binding of a Heparain–Mimicking Polyaromatic Anionic Compound", J. Amer. Soc. Nephrology, 1688–1697, 1997.

Miao et al. "Modulation of Fibroblast Growth Factor–2 Recptor Binding, Dimerization, Signal;ing, and Angiogenic Activity by a Synthetic Heparain–Mimicking Polyaromatic Compound", J. Clin. Invest., 99(7): 1565–1575, 1997.

Benezara et al., "Reversal of Fibroblast Growth Factor–mediated Autocrine Cell Transformation by Aromatic Aionic Compounds", Cancer Research, 52:5656–5662, 1992.

Irimura et al., "Chemically Modified Heparains as Inhibitors of Heparain Sulfarte Specific Endo–β–glucuronidase (Heparanse) of Metastatic melanoma Cells", Biochemistry, 25: 5322–5328, 1986.

(List continued on next page.)

Primary Examiner—Jon P. Weber
(74) Attorney, Agent, or Firm—Mark M. Friedman

(57) ABSTRACT

Qualitative and quantitative methods of testing an agent for its potential at inhibiting glycosidase catalytic activity, the methods including the steps of interacting a glycosidase enzyme with a glycosidase substrate in a presence of the agent and qualitatively or quantitatively evaluating an effect of the agent on the catalytic activity of the glycosidase enzyme toward the glycosidase substrate. Preferably the glycosidase enzyme is a heparanase enzyme and the glycosidase substrate is, respectively, a heparanase substrate.

61 Claims, 8 Drawing Sheets

OTHER PUBLICATIONS

DeVouge et al., "Immunoselection of GRP94/Endoplasmin From a KNRK Cell–Specific λgt11 Library Using Antobodies Directed Against a Putative Heparanse Amino–Terminal Peptide", Int. J. Cancer, 56: 286–294, 1994.

Orintz et al., "Heparin is Required for Cell–Free Binding of Basic Fibroblast Growth to a Soluble Receptor and for Mitogenesis in Whole Cells", Molecular and Cellular Biology, 12: 240–247, 1992.

Yayon et al., "Cell Surface, Heparin–like Molecules are Required for Binding of Basics Fibroblast Growth Factor to its High Affiinity Receptor", Cell, 64: 841–848, 1991.

Aviezer et al., "Differential Structural Requirements of Heparin Sulfate Proteoglycans That Promote Binding of Basic Fibroblast Growth to its Receptor", J. Biol. Chem., 269(1):114–121, 1994.

Bartlett et al., "Comparative Analysis of the Ability of Leucocytes, Endothelial Cells, and Platelets to Degrade the Subendothelial Basement Membrane: Evidence for Cytokine Dependence and Detection of a Novel Sulfatase", Immunolog†y and Cell Biol., 73: 113–124, 1995.

Zslonai et al., "Directional Immobiliztion of Heparin onto the Nonporous Surface of Polystyrene Micorplates", Biotechniques, 23(3): 382–385, 1997.

Bellott et al., "Closing the Loop in Combinational Chemistry", European Pharmaceutical Contractor, Aug., 1997.

Goldberg et al., "An Improved Method for Determining Proteoglycans Synthesis by Chondrocytesd in Culture", Live Tissue Research, 24: 265–275, 1990.

Voldavsky et al., "Extracellular Sequestration and Release of Fibroblast Growtrh Factor: A Regulartory Mechanism?", Trends Biochem. Sci., 16: 268–271, 1991.

Campbell et al., "Heparin Sulfate–Degrading Enzymes Induce Modulation of Smooth Muscle Phenotype"Exp. Cell Res., 200: 156–167, 1992.

Lider et al., "Suppression of Experimental Auto Diseases and Prolongation of Allograft Survival by Treatment of Animals with Low Doses of Heparin", J. Cli. Invest., 83: 752–756, 1989.

Thumberg et al., "The Molecular Size of the Antithrombin––Binding Sequence in Heparin", FEBS Letters, 117(1): 203–206, 1980.

Sudhalter et al., "Importance of Size, Sulfation and Antocoagulant Activity in the Acidic Fibroplast Growth Factor by Heparin", K. Biol. Chem., 254(12): 6892–6897, 1989.

Ishai–Michaeli et al., "Importance of Size and Sulfation of Heparin in Release of Basic Fibroplast Growth Factor from the Vascular Endothelium and Extracellular Matrix", Biochemistry, 31: 2080–2088, 1992.

Inoue et al., "Selective N–Desulfation of Heparin with Dimethyl Sulfoxide Containing Water or Methanol", Carbohydrate Research, 46:67–95, 1976.

Nagasawa et al., "Solvolytic Desulfation of Glycosaminoglycuronan Sulfates With Dimethyl Sulfoxide Containing Water or Methanol", Carbohydrate Research, 58: 47–55, 1977.

Matia Bar–New et al., "Inhibition of Heparanase–Mediated Degradation of Extracellular Matrix Heparin Sulfate by Non–Anticoogulant Heparin Speciec", Blood, 70(2): 551–557, 1987.

Gospodaarowic et al., "Stimulation of Corneal Endothelial Cell Proliferation in vitro by Fibroblast and Epidermal Growth Factors", Exp. Eye Res., 25: 75–89, 1977.

Haimovits–Fredman et al., "Activation pf Platelet Heparitinase by Tumor Cell–Derived Factors", Blood, 78: 789–796, 1991.

Voldavsky et al., "Extracellular Matrix–Resident Growth Factors and Enzymes: Possible Involvement in Tumor Metatastis and Angiogenesis", Cancer and Metatastis Rev., 9: 203–226, 1990.

Wright et al., "Role of Proteoglycans in Cell Adhesion, Migration and Proliferation", Cell Biology, 4: 93–801, 1992.

Jackson et al., "Glycosaminoglycans: Molecilar Properties, Protein Interaction, and Role in Physiological process", Physiological Review, 71(2):481–539, 1981.

Wight, T.N., "Cell Biology of Arterial Proteoglycans", Arteriosclerosis, 9(1):1–20, 1989.

Kjellen et al., "Proteoglycans: Structures and Interaction", Annu, Rev, Biochem., 60: 443–475, 1991.

Ruoslahati et al., "Proteoglycans as Modulators of Growth Factor Activities", Cell 64: 867–869, 1991.

Voldavsky et al., "Extracellular Matrix–Bound Growth Factors, Enzymes, and Plasma Proteins", In Basement Membranes: Cellular and Molecular Aspects, (eds,Rohrbach & Timpl), pp. 327–343, Academic Press Inc., Orlando, Fla., 1993.

Vlodavsky et al., "Expression of Heparanse by Platelets and Circulating Cells of the Immune System: Possible Involvement in Diapedesis and Extravasation", Invasion Metastis, 12: 112–127, 1992.

Voldavsky et al., "Inhibition of Tumor Metastasis by Heparanase Inhibiting Species of Heparin ",Jnvasion Metastasis, 14:290–302, 1994–95.

Nakajima et al., "Heparanase and Tumor Metastasis", J. Cellular Biochem., 36: 157–167, 1998.

Liotta et al., "Tumor Invasion and the Extracellular Matrix", Laboratory Investigation, 49)6):636–647, 1983.

Voldavasky et al., "Lymphom a Cell–Mediated Degradation of Sulfated Proteoglycans in the Subendothelial Extracellular Martix: Relationship to Tumor Cell Metastisis", Cancer Research, 43: 2704–2711, 1983.

Voldavsky et al., "Involvement of Heparanse in Tumor Metastasis and Angiogenesis"Isr, Med. Sci., 24: 464–470, 1983.

Parish et al., "Evidence That Sulphated Polysacacaridews Inhibit Tumor Metastasis by Blocking Tumour–Cell––Derived Heparanases", Int. J. Cancer, 40: 511–5187, 1987.

Voldavsaky et al., "Morphological Apperance, Growthh Behavior and Migratory Activity of Human Tumor Cells Mauntained on Extracellular Matrix Versus Plastic", Cell, 19: 607–616, 1980.

Wight et al., "The Role of Proteoglycans in Cell Adhesion, Migration and Proliferation", Cell Biology, 4: 93–801, 1992.*

Jackson et al., "Glycosaminoglycans: Molecular Properties, Protein Interactions, and Role in Physiological processes", Physiological Review, 71(2):481–539, 1981.*

Wight, T.N., "Cell Biology of Arterial Proteoglycans",Arteriosclerosis, 9(1):1–20, 1989.*

Kjellen et al, "Proteoglycans: Structures and Interactions", Annu. Rev. Biochem., 60: 443–475, 1991.*

Ruoslahti et al, "Proteoglycans as Modulators of Growth Factor Activities", Cell, 64: 867–869, 1991.*

Vlodavsky et al, "Extracellular Matrix–Bound Growth Factors, Enzymes, and Plasma Proteins", In Basement Membranes: Cellular and Molecular Aspects, (eds.Rohrbach & Timpl), pp 327–343, Academic Press Inc., Orlando, Fla., 1993.*

Vlodavsky et al., "Expression of Heparanase by Platelets and Circulating Cells of the Immune System: Possible Involvement in Diapedesis and Estravasation", Invasion Metastasis, 12:112–127, 1992.*

Vlodavsky et al, "Inhibition of Tumor Metastasis by Heparanase Inhibiting Species of Heparin", Invasion Metastasis, 14:290–302, 1994–95.*

Nakajima et al, "Heparanase and Tumor Metastasis", J. Cellular Biochem., 36:157–167, 1988.*

Liotta et al, "Tumor Invasion and the Extracellular Matrix", Laboratory Investigation, 49(6):636–647, 1983.*

Vlodavsky et al, "Lymphoma Cell–Mediated Degradation of Sulfated Proteoglycans in the Subendothelial Extracellular Matrix: Relationship to Tumor Cell Metastasis", Cancer Research, 43: 2704–2711, 1983.*

Vlodavsky et al, "Involvement of Heparanase in Tumor Metastasis and Angiogenesis" Isr. Med. Sci., 24: 464–470, 1983.*

Parish et al, "Evidence That Sulphated Polysaccarides Inhibit Tumor Metastasis by Blocking Tumour–Cell–Derived Heparanases", Int. J. Cancer, 40: 511–518, 1987.*

Vlodavsky et al, "Morphological Appearance, Growth Behavior and Migratory Activity in Human Tumor Cells Mauntained on Extracellular Matrix Versus Plastic", Cell, 19: 607–616, 1980.*

Vlodavsky et al, "Extracellular Sequestration and Release of Fibroblast Growtrh Factor: A Regulatory Mechanism?", Trends Biochem. Sci., 16: 268–271, 1991.*

Campell et al, "Heparin Sulfate–Degrading Enzymes Induce Modulation of Smooth Muscle Phenotype", Exp. Cell Res., 200: 156–167, 1992.*

Lider et al, "Suppression of Experimental Autoimmune Diseases and Prolongation of Allograft Survival by Treatment of Animals with Low Doses of Heparin", J. Clin. Invest., 83: 752–756, 1989.*

Thunberg et al, "The Molecular Size of the Antithrombin–Binding Sequence in Heparin", FEBS Letters, 117(1): 203–206, 1980.*

Sudhalter et al, "The Importance of Size, Sulfation and Anticoagulant Activity in the Potentiation of Acidic Fibroplast Growth Factor by Heparin", J. Biol. Chem., 254(12): 6892–6897, 1989.*

Ishai–Michaeli et al, "Importance of Size and Sulfation of Heparin in Release of Basic Fibroblast Growth Factor from the Vascular Endothelium and Extracellular Matrix", Biochemistry, 31: 2080–2088, 1992.*

Inoue et al, "Selective N–Desulfation of Heparin with Dimethyl Sulfoxide Containing Water or Methanol", Carbohydrate Research, 46:67–95, 1976.*

Nagasawa et al, "Solvolytic Desulfation of Glycosaminoglycuronan Sulfates With Dimethyl Sulfoxide Containing Water or Methanol", Carbohydrate Research, 58: 47–55, 1977.*

Matia Bar–New et al, "Inhibition of Heparanase–Mediated Degradation of Extracellular Matrix Heparin Sulfate by Non–Anticoagulant Heparin Species", Blood, 70(2): 551–557, 1987.*

Gospodarowicz et al, "Stimulation of Corneal Endothelial Cell Proliferation in vitro by Fibroblast and Epidermal Growth Factors", Exp. Eye Res., 25: 75–89, 1977.*

Haimovits–Friedman et al, "Activation of Platelet Heparitinase by Tumor Cell–Derived Factors", Blood, 78: 789–796, 1991.*

Vlodavsky et al, "Extracellular Matrix–Resident Growth Factors and Enzymes: Possible Involvement in Tumor Metatastis and Angiogenesis", Cancer and Metatastis Rev., 9: 203–226, 1990.*

Regan et al, "Mimicry of Biological Macromolecules by Polyaromatic Anionic Compounds", J. Bioactive and Compatible Polymers, 8:317–337, 1993.*

Benezra et al, "Antiproliferative Activity to Vascular Smooth Muscle Cells and Receptor Binding of Heparain–Mimicking Polyaromatic Anionic Compounds", Arteriosclerosis and Thrombosis, 14(12): 1992–1999, 1993.*

Katz et al, "Antiproliferative Activity to Glomerular Mesangial Cells and Receptor Binding of a Heparain–Mimicking Polyaromatic Anionic Compound", J. Amer. Soc. Nephrology, 1688–1697, 1997.*

Miao et al, "Modulation of Fibroblast Growth Factor–2 Receptor Binding, Dimerization, Signal;ing, and Angiogenic Activity by a Synthetic Heparain–Mimicking Polyaromatic Compound", J. Clin. Invest., 99(7): 1565–1575, 1997.*

Benezra et al, "Reversal of Fibroblast Growth Factor–mediated Autocrine Cell Transformation by Aromatic Anionic Compounds", Cancer Research, 52:5656–5662, 1992.*

Irimura et al, "Chemically Modified Heparins as Inhibitors of Heparin Sulfate Specific Endo–β–glucuronidase (Heparanase) of Metastatic melanoma Cells", Biochemistry, 25:5322–5328, 1986.*

Coombe et al, "Analysis of the Inhibition of Tumour Metastasis by Sulphated Polysaccharides", Int. J. Cancer, 39: 82–88, 1987.*

Ornitz et al, "Heparin is Required for Cell–Free Binding of Basic Fibroblast Growth Factor to a Soluble Receptor and for Mitogenesis in Whole Cells", Molecular and Cellular Biology, 12: 240–247, 1992.*

Yayon et al, "Cell Surface, Heparin–like Molecules are Required for Binding of Basic Fibroblast Growth Factor to its High Affinity Receptor", Cell, 64: 841–848, 1991.*

Aviezer et al, "Differential Structural Requirements of Heparin and Heparan Sulfate Proteoglycans That Promote Binding of Basic Fibroblast Growth Factor to its Receptor", J. Biol. Chem., 269(1):114–121, 1994.*

Bartlett et al, "Comparative Analysis of the Ability of Leucocytes, Endothelial Cells, and Platelets to Degrade the Subendothelial Basement Membrane: Evidence for Cytokine Dependence and Detection of a Novel Sulfatase", Immunology and Cell Biol., 73: 113–124, 1995.*

Nakajima et al, "A Solid–Phase Substarte of Heparanase: Its Application to Assay of Human Melanoma for Heparan Sulfate Degradative Activity", Analytical Biochemistry, 157: 162–171, 1986.*

Oosta et al, "Purification and Properties of Human Platalet Heparitanase, J. Biol. Chem.", 257(19): 11249–11255, 1982.*

Sewell et al, "Human Mononuclear Cells Contain an Endoglycosidase Specific for Heparan Sulfate Glycosaminoglycan Demonstrable with the Use of a Specific Solid–Phase Metabolically Radiolabelled Substrate", Biochem J., 264: 777–783, 1989.*

Freeman et al, "A Rapid Quantitative Assay for the Detection of Mammalian Heparanase Activity", *Biochem J.,* 325: 229–237, 1997.*

Mullings et al, "New Reducing Sugar Assay for the Study of Cellulases", *Enzyme Microb. Technol.,* 6:491–496, 1984.*

Taylor et al, "A colorimetric Method for Quantitation of Uronic Acids and a Specific Assay for Galacturonic Acid", *Analytical Biochemistry,* 201: 190–196, 1992.*

Linhardt, R.J., lary Electrophoresis of Oligosaccharides, *Methods of Enzymology,* 230: 265–280, 1994.*

Basu et al, "Analysis of Glycospingolipids by Fluorophore–Assisted Carbohydrate Electrophoresis Using Ceramide Glycanase from *Mercenaria mercenaria*", *Analytical Biochemistry,* 222:270–274, 1994.*

Jackson, P., "The Use of Polyacrylamide–gel Electrophoresis for the High–Resolution of Separation of Reducing Saccharides Labelled with the Fluorophore 8–aminoaphthalene–1,3,6–trisulphonic Acid", *Biochem J.,* 270: 705–713, 1990.*

Coquet et al, "Applications of a Post–column Fluorigenic Reaction in Liquid Chromotagraphy for the Determination of Glucose and Fructose in Biological Matrices", *Analytica Chemica Acta,* 252: 173–179, 1991.*

DeVouge et al, "Immunoselection of GRP94/Endoplasmin From a KNRK Cell–Specific λgt11 Library Using Antobodies Directed Against a Putative Heparanase Amino–Terminal Peptide", *Int. J. Cancer,* 56: 286–294, 1994.*

Zsolnai et al, "Directional Immobilization of Heparin onto the Nonporous Surface of Polystyrene Microplates", *Biotechniques,* 23(3):382–385, 1997.*

Bellott et al, "Closing the Loop in Combinatorial Chemistry", *European Pharmaceutical Contractor,* Aug., 1997.*

Goldberg et al, "An Improved Method for Determining Proteoglycans Synthesized by Chondrocytes in Culture", *Live Tissue Research,* 24: 265–275, 1990.*

Yen et al., "Potentialities of a New Class of Anticlotting and Antihemorrhagic Polymers", J. Macromol. Sci., Chem., 4(3), pp. 693–714 in Chem Abst. AN 1970:418456, 1970.*

Mes et al., "Use of Triphenyltetrazolium Chloride for the Quantitative Analysis of Sugars and Sugar Derivatives Reported in Glycoproteins", J. Chromatogr., 43(4), pp. 480–486, 1969.*

Mes et al., "Relative Sensitivity of Various Reagents for the Detection and Differentiation of Sugars and Sugar Derivatives in Glycoproteins", J. Chromatogr., 38(1), pp. 120–125, 1968.*

* cited by examiner

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 26
      (B) TYPE: nucleic acid
      (C) STRANDEDNESS: single
      (D) TOPOLOGY: linear (xi) SEQUENCE DESCRIPTION: SEQ ID NO: 1:

ACCATATGAA AAAGTTCAAG AACAGC                                       26

(2) INFORMATION FOR SEQ ID NO: 2:

(i) SEQUENCE CHARACTERISTICS:
      (A) LENGTH: 21
      (B) TYPE: nucleic acid
      (C) STRANDEDNESS: single
      (D) TOPOLOGY: linear (xi) SEQUENCE DESCRIPTION: SEQ ID NO: 2:

CAGCCACATA AAGCCAGCTG C                                                21

METHOD OF SCREENING FOR POTENTIAL ANTI-METASTATIC AND ANTI-INFLAMMATORY AGENTS USING MAMMALIAN HEPARANASE AS A PROBE

This is a continuation-in-part of U.S. patent application Ser. No. 09/109,386, filed Jul. 2, 1998, now abandoned, which is a continuation-in-part of U.S. patent application Ser. No. 08/922,170, filed Sep. 2, 1997, now U.S. Pat. No. 5,968,822, issued Oct. 19, 1999.

FIELD AND BACKGROUND OF THE INVENTION

The present invention relates to novel qualitative and quantitative glycosidases catalytic activity assays. More particularly, the present invention relates to a method of screening for potential anti-metastatic and anti-inflammatory agents and, most particularly, to a method of screening for potential anti-metastatic and anti-inflammatory agents using mammalian heparanase, preferably purified human recombinant heparanase, as a probe.

heparan sulfate proteoglycans (HSPGs): HSPGs are ubiquitous macromolecules associated with the cell surface and extracellular matrix (ECM) of a wide range of cells of vertebrate and invertebrate tissues (1–5). The basic HSPG structure consists of a protein core to which several linear heparan sulfate chains are covalently attached. The polysaccharide chains are typically composed of repeating hexuronic and D-glucosamine disaccharide units that are substituted to a varying extent with N- and O-linked sulfate moieties and N-linked acetyl groups (1–5). Studies on the involvement of ECM molecules in cell attachment, growth and differentiation revealed a central role of HSPGs in embryonic morphogenesis, angiogenesis, metastasis, neurite outgrowth and tissue repair (1–5). The heparan sulfate (HS) chains, which are unique in their ability to bind a multitude of proteins, ensure that a wide variety of effector molecules cling to the cell surface (4–6). HSPGs are also prominent components of blood vessels (3). In large vessels they are concentrated mostly in the intima and inner media, whereas in capillaries they are found mainly in the subendothelial basement membrane where they support proliferating and migrating endothelial cells and stabilize the structure of the capillary wall. The ability of HSPGs to interact with ECM macromolecules such as collagen, laminin and fibronectin, and with different attachment sites on plasma membranes suggests a key role for this proteoglycan in the self-assembly and insolubility of ECM components, as well as in cell adhesion and locomotion. Cleavage of HS may therefore result in disassembly of the subendothelial ECM and hence may play a decisive role in extravasation of normal and malignant blood-borne cells (7–9). HS catabolism is observed in inflammation, wound repair, diabetes, and cancer metastasis, suggesting that enzymes which degrade HS play important roles in pathologic processes.

Involvement of heparanase in tumor cell invasion and metastasis: Circulating tumor cells arrested in the capillary beds of different organs must invade the endothelial cell lining and degrade its underlying basement membrane (BM) in order to escape into the extravascular tissue(s) where they establish metastasis (10). Several cellular enzymes (e.g., collagenase IV, plasminogen activator, cathepsin B, elastase) are thought to be involved in degradation of the BM (10). Among these enzymes is an endo-β-D-glucuronidase (heparanase) that cleaves HS at specific intrachain sites (7, 9, 11–12). Expression of a HS degrading heparanase was found to correlate with the metastatic potential at mouse lymphoma (11), fibrosarcoma and melanoma (9) cells. The same is true for human breast, bladder and prostate carcinoma cells (see U.S. pat application Ser. No. 09/109,386, which is incorporated by reference as if fully set forth herein). Moreover, elevated levels of heparanase were detected in sera (9) and urine (U.S. patent application Ser. No. 09/109,386,) of metastatic tumor bearing animals and cancer patients and in tumor biopsies (12). Treatment of experimental animals with heparanase alternative substrates and inhibitor (e.g., non-anticoagulant species of low MW heparin, laminarin sulfate) markedly reduced (>90%) the incidence of lung metastases induced by B16 melanoma, Lewis lung carcinoma and mammary adenocarcinoma cells (8, 9, 13), indicating that heparanase inhibitors may be applied to inhibit tumor cell invasion and metastasis.

Our studies on the control of tumor progression by its local environment, focus on the interaction of cells with the extracellular matrix (ECM) produced by cultured corneal and vascular endothelial cells (EC) (14, 15). This ECM closely resembles the subendothelium in vivo in its morphological appearance and molecular composition. It contains collagens (mostly type III and IV, with smaller amounts of types I and V), proteoglycans (mostly heparan sulfate- and dermatan sulfate-proteoglycans, with smaller amounts of chondroitin sulfate proteoglycans), laminin, fibronectin, entactin and elastin (13, 14). The ability of cells to degrade HS in the ECM was studied by allowing cells to interact with a metabolically sulfate labeled ECM, followed by gel filtration (Sepharose 6B) analysis of degradation products released into the culture medium (11). While intact HSPG are eluted next to the void volume of the column (Kav<0.2, Mr of about $0.5 \times 10^6$), labeled degradation fragments of HS side chains are eluted more toward the Vt of the column (0.5<kav<0.8, Mr of about $5-7 \times 10^3$) (11). Compounds which efficiently inhibit the ability of heparanase to degrade the above-described naturally produced basement membrane-like substrate, were also found to inhibit experimental metastasis in mice and rats (8, 9, 13, 33). A reliable in vitro screening system for heparanase inhibiting compounds may hence be applied to identify and develop potent anti-metastatic drugs.

Possible involvement of heparanase in tumor angiogenesis: We have previously demonstrated that heparanase may not only function in cell migration and invasion, but may also elicit an indirect neovascular response (15). Our results suggest that the ECM HSPGs provide a natural storage depot for PFGF and possibly other heparin-binding growth promoting factors. Heparanase mediated release of active βFGF from its storage within ECM may therefore provide a novel mechanism for induction of neovascularization in normal and pathological situations (6, 18).

Expression of heparanase by cells of the immune system: Heparanase catalytic activity correlates with the ability of activated cells of the immune system to leave the circulation and elicit both inflammatory and autoimmune responses. Interaction of platelets, granulocytes, T and B lymphocytes, macrophages and mast cells with the subendothelial ECM is associated with degradation of heparan sulfate (HS) by heparanase catalytic activity (7). The enzyme is released from intracellular compartments (e.g., lysosomes, specific granules) in response to various activation signals (e.g., thrombin, calcium ionophore, immune complexes, antigens, mitogens), suggesting its regulated involvement and presence in inflammatory sites and autoimmune lesions. Heparan sulfate degrading enzymes released by platelets and macrophages are likely to be present in atherosclerotic lesions (16). Treatment of experimental animals with heparanase alternative substrates (e.g., non-anticoagulant species of low molecular weight heparin) markedly reduced the incidence of experimental autoimmune encephalomyelitis (EAE), adjuvant arthritis and graft rejection (7, 17) in experimental animals, indicating that heparanase inhibitors may be applied to inhibit autoimmune and inflammatory diseases (7, 17). A reliable in vitro screening system for heparanase inhibiting compounds may hence be applied to identify and develop non-toxic anti-inflammatory drugs for the treatment of multiple sclerosis and other inflammatory diseases.

Cloning and expression of the heparanase gene: A purified fraction of heparanase isolated from human hepatoma cells was subjected to tryptic digestion. Peptides were separated by high pressure liquid chromatography and micro sequenced. The sequence of one of the peptides was used to screen data bases for homology to the corresponding back translated DNA sequence. This procedure led to the identification of a clone containing an insert of 1020 base pairs (bp) which included an open reading frame of 963 bp followed by 27 bp of 3' untranslated region and a poly A tail. The new gene was designated hpa. Cloning of the missing 5' end of hpa was performed by PCR amplification of DNA from placenta cDNA composite. The entire heparanase cDNA was designated phpa. The joined cDNA fragment contained an open reading frame which encodes a polypeptide of 543 amino acids with a calculated molecular weight of 61,192 daltons. Cloning an extended 5' sequence was enabled from the human SK-hep1 cell line by PCR amplification using the Marathon RACE system. The 5' extended sequence of the SK-hep1 hpa cDNA was assembled with the sequence of the hpa cDNA isolated from human placenta. The assembled sequence contained an open reading frame which encodes a polypeptide of 592 amino acids with a calculated molecular weight of 66,407 daltons. The cloning procedures are described in length in U.S. patent application Ser. No. 09/109,386.

The ability of the hpa gene product to catalyze degradation of heparan sulfate (HS) in vitro was examined by expressing the entire open reading frame of hpa in High five and Sf21 insect cells, and the mammalian human 293 embryonic kidney cell line expression systems. Extracts of infected cells were assayed for heparanase catalytic activity. For this purpose, cell lysates were incubated with sulfate labeled, ECM-derived HSPG (peak I), followed by gel filtration analysis (Sepharose 6B) of the reaction mixture. While the substrate alone consisted of high molecular weight material, incubation of the HSPG substrate with lysates of cells infected with hpa containing virus resulted in a complete conversion of the high molecular weight substrate into low molecular weight labeled heparan sulfate degradation fragments (U.S. Pat. application Ser. No. 09/109,386).

In subsequent experiments, the labeled HSPG substrate was incubated with the culture medium of infected High Five and Sf21 cells. Heparanase catalytic activity, reflected by the conversion of the high molecular weight HSPG substrate into low molecular weight HS degradation fragments, was found in the culture medium of cells infected with the pFhpa virus, but not the control pF1 virus.

Altogether, these results indicate that the heparanase enzyme is expressed in an active form by cells infected with Baculovirus or mammalian expression vectors containing the newly identified human hpa gene.

In other experiments, we have demonstrated that the heparanase enzyme expressed by cells infected with the pFhpa virus is capable of degrading HS complexed to other macromolecular constituents (e.g., fibronectin, laminin, collagen) present in a naturally produced intact ECM (09/109,386), in a manner similar to that reported for highly metastatic tumor cells or activated cells of the immune system (7, 8)

Purification of the recombinant heparanase enzyme: Sf21 insect cells were infected with pFhpa virus and the culture medium was applied onto a heparin-Sepharose column. Fractions were eluted with a salt gradient (0.35–2.0 M NaCl) and tested for heparanase catalytic activity and protein profile (SDS/PAGE followed by silver staining). Heparanase catalytic activity correlated with the appearance of a about 63 kDa protein band in fractions 19–24, consistent with the expected molecular weight of the hpa gene product. Active fractions eluted from heparin-Sepharose were pooled, concentrated and applied onto a Superdex 75 FPLC gel filtration column. Aliquots of each fraction were tested for heparanase catalytic activity and protein profile. A correlation was found between the appearance of a major protein (approximate molecular weight of 63 kDa) in fractions 4–7 and heparanase catalytic activity. This protein was not present in medium conditioned by control non-infected Sf21 cells subjected to the same purification protocol. Recently, an additional purification protocol was applied, using a single step chromatography with source-S ion exchange column. This purification resulted in a purified protein to a degree of 90%. Further details concerning theses purification procedure are disclosed in U.S. patent applicaiton Ser. Nos. 09/109,386 and 09/071,618, both are incorporated by reference as if fully set forth herein.

Recombinant heparanase for screening purposes: Research aimed at identifying and developing inhibitors of heparanase catalytic activity has been handicapped by the lack of a consistent and constant source of a purified and highly active heparanase enzyme and of a reliable screening system. Our recent cloning, expression and purification of the human heparanase-encoding gene offer, for the first time, a most appropriate and reliable source of active recombinant enzyme for screening of anti-heparanse antibodies and compounds which may inhibit the enzyme and hence be applied to identify and develop drugs that may inhibit tumor metastasis, autoimmune and inflammatory diseases.

Screening for specific inhibitors using a combinatorial library: A new approach aimed at rational drug discovery was recently developed for screening for specific biological activities. According to the new approach, a large library of chemically diversed molecules are screened for the desired biological activity. The new approach has become an effective and hence important tool for discovery of new drugs. The new approach is based on "combinatorial" synthesis of a diverse set of molecules in which several components predicted to be associated with the desired biological activity are systematically varied. The advantage of a combinatorial library over the alternative use of natural extracts for screening for desired biologically active compounds is that all the components comprising the library are known in advance (50).

In combinatorial screening, the number of hits discovered is proportional to the number of molecules tested. This is true even when knowledge concerning the target is unavailable. The large number of compounds, which may reach thousands of compounds tested per day, can only be screened, provided that a suitable assay involving a high throughput screening technique, in which laboratory automation and robotics may be applied, exists.

Prior art heparanase catalytic activity assays: Several methods for determining heparanase catalytic activity have been developed throughout the years. All of the different methods are based on radiolabeling of a substrate (either in vitro or metabolically, as described above) and analysis of its degradation products released due to heparanase catalytic activity. These prior art methods suffer several disadvantages and limitations as follows.

First, the measurement of catalytic activity is qualitative and not quantitative. This is due to the following reasons (i) the radioactive labeling is not spread evenly along the substrate chain, therefore, radioactivity may not correlate precisely with activity; (ii) since heparanase substrates are long substrate chains, a released product can be, in fact, a substrate of heparanase, however while executing any of the prior art methods, cleavage events of released products are not monitorable. Moreover, multiple cleavage events of small portions of the substrate chain are indistinguishable from fewer cleavage events, yet of longer substrate chains. Thus, not all, and in many cases, depending on the substrate chain length, not even most, of the cleavage events catalyzed by the enzyme are detectable, thereby affecting the linearity of the assay.

Second, the prior art methods are cumbersome, time-consuming and do not allow activity determination of a large number of samples simultaneously. In most cases, both preparation of the radiolabeled substrate and separation of the degradation products from the uncleaved substrate involve long and complex procedures and handling with radioactive material which calls strict safety procedures.

Third, all of the prior art methods for determining heparanase catalytic activity involve modification of the substrate by either iodination at glucosamine residues, or either O- or N-acetylation of the partially de-N-sulfated substrate. Such procedures may result in masking heparanase cleavage sites, or alternatively creating new heparanase sites.

The different prior art methods also have specific disadvantages specifically associated with each of which. Some methods involve biosynthetic radiolabeling of ECM associated HSPG and detection of HS chain degradation by gel filtration analysis of the radiolabeled material released from the labeled ECM (7, 37). In these assays, detection of the products requires a synergistic activity of proteases and heparanase. Protease is required to expose HS chains to cleavage by heparanase.

Other methods involve immobilizing chemically or biosynthetically radiolabeled heparanase substrate chains (38, 39, 40). The main disadvantage of these methods is that the immobilized substrate may be less accessible to the enzyme.

In the heparanase catalytic activity assay recently developed by Freeman and Parish (41) the products are separated from the substrate by binding to chicken histidine-rich glycoprotein (cHRG) sepharose. In this method only the lowest molecular weight products that lose the ability to bind to cHRG sepharose are detectable, while other, longer, products bind to the column with the substrate and are therefore excluded.

The mechanism by which heparanase operates on its substrate is still unknown and it is possible that some chains may first be cleaved to longer chains and then further be degraded to smaller fragments, while other chains may be directly cleaved at the end of thereof to form small fragments. The method by Freeman and Parish, therefore, fails to detect all of the cleavage products and therefore, like all of the other prior art methods for assaying heparanase catalytic activity, it is qualitative rather than quantitative.

The lack of a quantitative heparanase catalytic activity assay combined with the time and labor required to analyze a single sample using the qualitative prior art methods highlights the need for a rapid quantitative heparanase catalytic activity assay capable of assaying a large number of samples simultaneously.

SUMMARY OF THE INVENTION

According to one aspect of the present invention there is provided a method of testing an agent for its potential at inhibiting heparanase catalytic activity, the method comprising the steps of interacting a recombinant heparanase enzyme with a heparanase substrate in a presence of the agent and evaluating an effect of the agent on the catalytic activity of the recombinant heparanase enzyme toward the heparanase substrate.

According to another aspect of the present invention there is provided a method of screening for agents inhibiting heparanase catalytic activity and hence potentially inhibiting tumor metastasis, autoimmunity and inflammatory diseases, the method comprising the steps of, in individual reactions, interacting a recombinant heparanase enzyme with a heparanase substrate in a presence of each of the agents and evaluating an effect of each of the agents on the catalytic activity of the recombinant heparanase enzyme toward the heparanase substrate.

According to yet another aspect of the present invention there is provided a quantitative method of testing an agent for its potential at inhibiting glycosidase catalytic activity, the method comprising the steps of interacting a glycosidase enzyme with a glycosidase substrate in a presence of the agent and quantitatively evaluating an effect of the agent on the catalytic activity of the glycosidase enzyme toward the glycosidase substrate. Preferably the glycosidase enzyme is a heparanase enzyme and the glycosidase substrate is, respectively, a heparanase substrate.

According to still another aspect of the present invention there is provided a method of screening for agents inhibiting heparanase catalytic activity and hence potentially inhibiting tumor metastasis, autoimmunity and inflammatory diseases, the method comprising the steps of, in individual reactions, interacting a heparanase enzyme with a heparanase substrate in a presence of each of the agents and quantitatively evaluating an effect of each of the agents on the catalytic activity of the heparanase enzyme toward the heparanase substrate.

According to still another aspect of the present invention there is provided a method of testing heparanase catalytic activity, the method comprising the steps of interacting a recombinant heparanase enzyme with a heparanase substrate and evaluating the catalytic activity of the recombinant heparanase enzyme toward the heparanase substrate.

According to still another aspect of the present invention there is provided a quantitative method of testing glycosidase catalytic activity, the method comprising the steps of interacting a glycosidase enzyme with a glycosidase substrate and quantitatively evaluating the catalytic activity of the glycosidase enzyme toward the glycosidase substrate.

According to further features in preferred embodiments of the invention described below, the glycosidase or heparanase (including recombinant heparanase) are each independently of a human origin.

According to still further features in the described preferred embodiments the heparanase is a natural heparanase.

According to still further features in the described preferred embodiments the recombinant heparanase is expressed in an expression system selected from the group consisting of an insect cell expression system, a mammalian cell expression system and a yeast cell expression system.

According to still further features in the described preferred embodiments the substrate is radiolabeled.

According to still further features in the described preferred embodiments the radiolabeled substrate is radiolabeled by a radiolabeling method selected from the group consisting of in vitro radiolabeling and metabolically radiolabeling.

According to still further features in the described preferred embodiments the substrate is an extracellular matrix or a portion thereof.

According to still further features in the described preferred embodiments the substrate includes macromolecules associated with the extracellular matrix.

According to still further features in the described preferred embodiments the macromolecules include heparan sulfate proteoglycans. In other words, the substrate preferably includes extracellular matrix-derived soluble heparan sulfate proteoglycans.

According to still further features in the described preferred embodiments the substrate is selected from the group consisting of heparan sulfate, heparin, heparin-sepharose, and derivatives thereof.

According to still further features in the described preferred embodiments the substrate is immobilized to a solid support, e.g., heparin-sepharose.

According to still further features in the described preferred embodiments the agent or agents include an anti-heparanase antibody.

According to still further features in the described preferred embodiments the agent or agents include a naturally occurring agent.

According to still further features in the described preferred embodiments the agent or agents include a synthetic agent.

According to still further features in the described preferred embodiments the synthetic agent is one of a plurality of agents belonging to a combinatorial library of similar agents.

According to still further features in the described preferred embodiments evaluating the effect of the agent or agents on the catalytic activity of the recombinant heparanase enzyme toward the heparanase substrate is effected by a size separation assay adapted for detection of degradation products of the heparanase substrate.

According to still further features in the described preferred embodiments the size separation assay is selected from the group consisting of gel electrophoresis and column chromatography.

According to still further features in the described preferred embodiments quantitatively evaluating the effect the catalytic activity of the glycosidase enzyme toward the glycosidase substrate and the effect of the agent or agents thereupon is effected by an assay adapted for detection of reducing moieties associated with degradation products of the glycosidase substrate.

According to still further features in the described preferred embodiments quantitatively evaluating the catalytic activity of the glycosidase enzyme toward the glycosidase substrate and the effect of the agent or agents thereupon is effected by a calorimetric assay.

According to still further features in the described preferred embodiments quantitatively evaluating the catalytic activity of the heparanase enzyme toward the heparanase substrate and the effect of the agent or agents thereupon is effected by an assay adapted for detection of reducing moieties associated with degradation products of the heparanase substrate.

According to still further features in the described preferred embodiments the assay is a reducing sugar assay.

According to still further features in the described preferred embodiments the colorimetric assay is a tetrazolium blue assay in which tetrazolium blue is reduced to a soluble colored formazan salt.

According to still further features in the described preferred embodiments the method behaves substantially linearly in a range of enzyme concentration.

According to still further features in the described preferred embodiments the method behaves substantially linearly in a range of time.

According to still further features in the described preferred embodiments the colorimetric assay is selected from the group consisting of carbazole assay and methylene blue assay.

The present invention successfully addresses the shortcomings of the presently known configurations by providing in one aspect, novel calorimetric qualitative and quantitative heparanase (and other glycosidases) activity assays. The qualitative assays are base on calorimetric detection of uronic (e.g., iduronic) acids in a complete hydrolyzate of the products released by heparanase catalytic activity acting on an immobilized substrate (e.g., heparin-sepharose), or on calorimetric detection of sulfated glycosaminoglycans similarly released from the immobilized substrate. It is therefore easier to implement as compared to the radioactive methods which call for size separation and like the radioactive methods it is applicable for activity determinations of crude enzyme extracts, as well as purified enzyme.

The quantitative assay is based on detection of newly formed reducing ends produced due to cleavage of polysaccharides, such as, but not limited to, heparin or heparan sulfate by glycosidases. This assay therefore detects every single cleavage event and can be used to extract activity catalytic constants of the enzyme and of inhibitors/activators thereof. The new assays allow for efficient screening of a large number of different agents simultaneously for their inhibitory effects on the enzyme. More specifically, these assays can be used to screen for potential inhibitors of heparanase and other glycosidases, by, for example, using recombinant heparanase combined with heparan sulfate or heparin as a substrate.

BRIEF DESCRIPTION OF THE DRAWINGS

The invention herein described, by way of example only, with reference to the accompanying drawings, wherein:

FIG. 8 demonstrates polyacrylamide gel analysis of heparanase catalytic activity with heparin-sepharose as a substrate. Heparin-sepharose was incubated (37° C., 24 hours, pH 5.4) in the presence or absence of recombinant heparanase. The products were analyzed by fractionation on a native acrylamide gel stained with methylene blue. Lane A—heparin-sepharose control. Lane B—heparin-sepharose incubated with the recombinant heparanase. Heparanase catalytic activity may be visualized as a sift in the mobility of the products as compared to the substrate.

DESCRIPTION OF THE PREFERRED EMBODIMENTS

Figure 1:
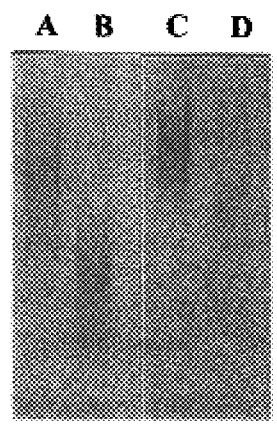
FIG. 1 demonstrates polyacrylamide gel analysis of heparanase catalytic activity. Heparin and heparan sulfate were incubated (24 hours, 37° C., pH 5.4) with human recombinant heparanase enzyme. Following incubation, degradation products were fractionated on an acrylamide gel and were stained with methylene blue. Lane A—heparin control; lane B—heparin incubated with the recombinant heparanase; lane C—heparan sulfate control; lane D—heparan sulfate incubated with the recombinant heparanase.

The present invention is of a method of screening for heparanase inhibitors which can be used for identifying potential anti-metastatic and anti-inflammatory agents. Specifically, the present invention provides novel qualitative and quantitative colorimetric assays for assaying heparanase catalytic activity.

The principles and operation of the method according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Several studies have shown that heparanase catalytic activity expressed by either normal or neoplastic cells can be effectively inhibited by heparin, modified non-anticoagulant species of heparin and other sulfated polysaccharides (e.g., pentosan polysulfate) and polyanionic molecules (oligonucleotides) (8, 9, 13, 23). Moreover, there was a reasonable good correlation between the heparanase inhibiting activity of these compounds and their ability to inhibit tumor metastasis and inflammatory diseases in experimental animals (8, 13, 17).

The inhibitory effect of heparin on the heparanase enzyme activity is caused presumably due to its being an alternative substrate of the enzyme, as shown in FIG. 1. The presence of an alternative substrate which may be more accessible to the enzyme could decrease the catabolism of the ECM by heparanase.

Although many of the inhibitory compounds were anticoagulants, the anti-metastatic and anti-inflammatory potential at the molecules did not correlate with their anticoagulant activity (8, 13, 17, 32). Moreover, inhibitory polysaccharides did not affect adhesion of tumor cells to the vascular endothelium (33). Parish et al. (13) have demonstrated that sulfated polysaccharides inhibit metastatic dissemination of rat mammary adenocarcinoma cells by inhibiting tumor-cell-derived heparanases involved in the penetration of the vascular endothelium and its underlying basement membrane by tumor cells (13). It is therefore highly important to develop appropriate tools to screen for heparanase inhibiting molecules.

The results described herein in the Examples section emphasize the feasibility of using a both crude and purified human recombinant heparanase to screen, using simple colorimetric assays, polyanionic molecules, chemically modified species of heparin size homogeneous oligosaccharides derived from depolymerized heparin, libraries of small molecules and rationally designed molecules for anti-heparanase catalytic activity.

Compounds that inhibited heparanase mediated degradation of heparan sulfate in intact ECM were also found to be potent inhibitors of B16 melanoma and breast carcinoma lung colonization (8), see Table 1 below. These compounds also inhibited several inflammatory diseases (7, 17), pointing toward the clinical significance of the screening method described herein.

TABLE 1

| Compound | Inhibition | |
|---|---|---|
| | heparanase | lung colonization |
| heparin fragment | + | + |
| N-hexanoyl heparin | + | + |
| heparin-tetrasaccharide | – | – |
| heparin tetradeca-saccharide | + | + |
| totally desulfated heparin | – | – |

Effect of heparin species on lung colonization of B16–BL6 melanoma cells. C57BL mice received a single subcutaneous injection of 400 µg/ml of heparin fragment, N-hexanoyl heparin fragment, heparin derived tetrasaccharide, heparin derived tetradeca-saccharide, or totally desulfated fragmin, followed by an intravenous inoculation of B16–BL6 cells ($10^5$ cells/mouse). Fifteen days afterwards the mice were sacrificed and the lungs fixed in Bouen's solution.

We have demonstrated herein that inhibition of heparanase and tumor metastasis was achieved by heparin species containing 14 sugar units or more and having sulfate groups at both the N and O positions (8). Low sulfate oligosaccharides were less effective heparanase inhibitors than medium and high sulfate fractions of the same size. While O-desulfation abolished the heparanase inhibiting effect of heparin, N-acetylated or N-hexonyl heparin retained a high inhibitory activity, provided that the N-substituted molecules had a molecular size of about 4,000 Dalton or more (8).

We have previously demonstrated that the presence of N-sulfates is a critical requirement for release of ECM-bound βFGF by species of heparin (20). It was found that total substitution of N-sulfates with acetyl or hexanoyl groups resulted in an almost complete inhibition of the βFGF-releasing activity of heparin, despite a normal content of O-sulfate groups (20). Unlike the inhibition of heparanase catalytic activity and lung colonization, a nearly maximal release of ECM-bound βFGF was obtained already by the octasaccharide, while the tetrasaccharide exhibited about 40% of the activity of intact heparin when compared on a weight basis (20). No correlation was found between the antithrombotic activity (anti-factor Xa activity) of heparin and its anti-metastatic and βFGF-releasing activities, indicating that the specific pentasaccharide sequence responsible for the binding of anticoagulant heparin to antithrombin III is not required for inhibition of heparanase and release of ECM-bound βFGF.

Heparin or heparan sulfate proteoglycans are involved in receptor binding and mitogenic activity of βFGF (34, 35). We have previously investigated the capacity of various species of heparin and HS to promote β FGF receptor binding using both CHO mutant cells deficient in cell surface is HSPG and a soluble βFGF receptor-alkaline phosphatase fusion protein (36). There was an absolute requirement for O-sulfation and a synergistic effect of N-linked sulfates. These structural characteristics of heparin are distinct from those sufficient for displacement of βFGF bound to HS on cell surfaces and ECM (20).

Altogether, these results indicate that different effects of heparin are mediated by different sugar sequences and that unique heparin-like molecules can be designed to elicit or inhibit a specific function. For example, N-substituted species of heparin and in particular N-hexanoyl heparin fragment, rather than native heparin, could be applied to inhibit tumor metastasis, since their efficient inhibition of heparanase catalytic activity was not associated with a significant release of active βFGF from cells and ECM.

These compounds are therefore expected to inhibit metastases formation and inflammatory diseases, correlated with their inhibition of heparanase catalytic activity, with little or no potential induction of neovascularization in response to βFGF release. Similarly, our synthetic polyanionic compounds may exhibit differential activities, provided that appropriate screening systems will be applied. As demonstrated herein, the availability of a recombinant heparanase enzyme and unique heparanase assay systems, can be used to identify specific heparanase inhibiting agents. The most potent compounds may then be tested for clinical efficacy in vivo.

Assays utilizing a radiolabeled substrate can not differentiate between an inhibitory effect of a compound and its being an alternative substrate. In these assays only radiolabeled products are detected, while non-labeled products of an alternative substrate can not be detected. We have modified a simple and convenient semi-quantitative gel analysis (48) in which the substrate as well as its degradation products mediated through heparanase catalytic activity may be visualized on a gel. This method may be used to qualitatively identify heparanase catalytic activity, and also as a simple tool for examining substrate utilization by the enzyme.

Another method presented is the use of an immobilized substrate (heparin-sepharose) and detection of the soluble reaction products by either the calorimetric carbazole or dimethylmethylene blue assays. Similarly, the substrate may be immobilized to microplates such as carbo or hydrazido plates (49). The advantages of these methods are that the activity may be determined using any source of enzyme and not specifically a purified enzyme. Furthermore, these methods do not involve the use of radiolabeled substrates and they obviate the need for size separation. However, these methods are qualitative in nature because, in the carbazole assay, for example, the detection is of uronic (e.g., iduronic) acids present in a complete hydrolyzate of the products released by heparanase acting on the immobilized substrate. The dimethylmethylene blue assay is similarly qualitative because it detects sulfated glycosaminoglycans released from the immobilized substrate, regardless of their size.

Previous assays developed for the detection of heparanase catalytic activity utilized radiolabeling of the substrate. All these assays are not quantitative, not accurate, they are all time consuming and are not suitable for rapid screening of large number of inhibitors. Here we further describe an assay based on a the detection of newly made reducing ends produced by each cleavage action of the enzyme.

This assay has several advantages over the existing assays and also over the qualitative carbazole and dimethylmethylene blue assays:

First, it allows accurate quantification of heparanase catalytic activity due to detection of any newly formed reducing ends produced by each cleavage action of the enzyme.

Second, the method is rapid, is not time consuming, simple and does not involve time consuming and difficult preparations of the substrate or separation of the reaction products from the substrate.

Third, the substrate is soluble and therefore is accessible to the enzyme.

Fourth, The substrate is used without undergoing any modifications which may mask or create new cleavage sites for heparanase.

Fifth, the method does not involve the use of radioactive or hazardous materials.

Sixth, the method allows screening of a large number of samples simultaneously.

Seventh, the method utilizes conventional laboratory equipment (e.g., 96 well microplates, microplate reader).

Eighth, the method distinguishes between inhibitory activity of a given compound and its being an alternative substrate.

All these advantages make this assay highly suitable for screening potential anti-metastatic and anti-inflammatory inhibitors using the recombinant mammalian heparanase.

To increase the sensitivity of the assay, the newly formed reducing ends produced by the heparanase may be detected using a fluorigenic reaction with a compound which gives a shift in fluorescence upon reduction (47), such as benzamidine (47) or ANTS (44, 45, 46).

This method in which newly formed reducing ends are detected in microplates may be extended to detect the activity of any enzyme which produces reducing ends, such as glucoronidase, chondroitinase, hyaloronidase, neuraminidase, galactosidase, etc., provided a purified enzyme and substrate are used.

Thus in accordance with one aspect of the teachings of the present invention there is provided a method of testing an agent for its potential at inhibiting heparanase catalytic activity. The method is effected by implementing the following method steps, in which in a first step a recombinant heparanase enzyme is interacted with a heparanase substrate in the presence of the agent, whereas in a subsequent step of the method the effect of the agent on the catalytic activity of the recombinant heparanase enzyme toward the heparanase substrate is evaluated.

According to another aspect of the present invention there is provided a method of screening for agents inhibiting heparanase catalytic activity and hence potentially inhibiting tumor metastasis, autoimmunity and inflammatory diseases. The method is effected by implementing the following method steps, in which in a first step, a recombinant heparanase enzyme is interacted, in individual reactions, with a heparanase substrate in a presence of each of the agents, whereas in a subsequent step of the method the effect of each of the agents tested on the catalytic activity of the recombinant heparanase enzyme toward the heparanase substrate is evaluated.

According to yet another aspect of the present invention there is provided a quantitative method of testing an agent for its potential at inhibiting glycosidase catalytic activity. The method is effected by implementing the following method steps, in which in a first step a glycosidase enzyme is interacted with a glycosidase substrate in a presence of the agent, whereas in a subsequent step of the method the effect of the agent on the catalytic activity of the glycosidase enzyme toward the glycosidase substrate is quantitatively evaluated.

According to still another aspect of the present invention there is provided a method of screening for agents inhibiting heparanase catalytic activity and hence potentially inhibiting tumor metastasis, autoimmunity and inflammatory diseases. The method is effected by implementing the following method steps, in which in a first step a heparanase enzyme is interacted, in individual reactions, with a heparanase substrate in a presence of each of the agents, whereas in a subsequent step of the method the effect of each of the agents on the catalytic activity of the heparanase enzyme toward the heparanase substrate is quantitatively evaluated.

According to an additional aspect of the present invention there is provided a quantitative method of testing glycosidase catalytic activity. The method the method is effected by implementing the following method steps, in which in a first step a glycosidase enzyme is interacted with a glycosidase substrate, whereas in a subsequent step of the method the catalytic activity of the glycosidase enzyme toward the glycosidase substrate is quantitatively evaluated.

As used herein in the specification, the term "qualitative" may also refer to semi-quantitative.

As used herein in the specification and in the claims section below, the phrase "glycosidase catalytic activity" refers to an animal endoglycosidase hydrolyzing activity.

As used herein in the specification and in the claims section below, the phrase "glycosidase enzyme" refers to an enzyme having glycosidase catalytic activity. Examples include, but are not limited to, heparanase and types of glucoronidases, chondroitinase, hyaloronidase, neuraminidase, galactosidase, etc.

As used herein in the specification and in the claims section below, the phrase "heparanase catalytic activity" refers to an animal endoglycosidase hydrolyzing activity which is specific for heparin or heparan sulfate proteoglycan substrates, as opposed to the activity of bacterial enzymes (heparinase I, II and III) which degrade heparin or heparan sulfate by means of β-elimination.

As used herein in the specification and in the claims section below, the phrase "heparanase enzyme" refers to an enzyme having heparanase catalytic activity. Examples include human or any other natural mammalian heparanase which can be purified following the method described in U.S. Pat. No. 5,362,641 to Fuks, which is incorporated by reference as if fully set forth herein, or preferably recombinant mammalian heparanase, the gene for which, and the expression and purification of which are described in length in U.S. patent application Ser. Nos. 09/109,386 and 09/071,618. It will be appreciated by one ordinarily skilled in the art that using the human heparanase gene sequence one can readily clone, express and purify recombinant heparanase of any other mammal. This sequence of events, i.e., cloning a gene of one species based on the sequence of the same gene from another species, proved successful in hundreds of previous cases, especially since the polymerase chain reaction (PCR) is practiced therefore.

As used herein in the specification and in the claims section below, the phrase "recombinant heparanase enzyme" refers to an enzyme whose coding sequence has been cloned and is expressed in an expression system.

As used herein in the specification and in the claims section below, the phrase "heparanase substrate" or "glycosidase substrate" refers to a substrate cleavable into degradation products by the respective enzymes.

As used herein in the specification and in the claims section below, the phrases "inhibiting heparanase catalytic activity" or "inhibiting glycosidase catalytic activity" refers an inhibition of the catalytic activity of the respective enzyme toward a specific substrate in a given assay. Thus, both (other) substrates and inhibitors qualify for inhibiting the catalytic activity of the respective enzymes.

As used herein in the specification and in the claims section below, the phrases "interacted" also means contacted under reaction favorable conditions, i.e., conditions which allow the progress of the reaction to yield reaction products in the absence of inhibition.

The expression system used to express recombinant heparanase according to the present invention may be any suitable expression system. Examples include, but are not limited to, insect cell expression systems, mammalian cell expression systems, and yeast cell expression systems, however, bacterial expression systems are not excluded, see U.S. patent application Ser. No. 09/071,618.

The substrate used according to one aspect of the method of the present invention is radiolabeled, using, for example, a radiolabeling method, such as but not limited to in vitro radiolabeling and metabolically radiolabeling.

According to one embodiment of the present invention the substrate is an extracellular matrix or a portion thereof. The substrate preferably includes macromolecules associated with the extracellular matrix, such as, but not limited to, heparan sulfate proteoglycans, the natural substrate of various glycosidases including heparanase.

However, according to a presently preferred embodiment of the present invention the substrate is heparan sulfate, heparin, heparin-sepharose, or derivatives thereof.

The agent or agents screened for can be of any type. One example include anti-heparanase antibodies. It is well known that by binding to the active site antibodies can be used to inhibit catalytic activity of an enzyme.

As used herein in the specification and in the claims section below, the term "antibody" refers to any monoclonal or polyclonal immunoglobulin, or a fragment of an immunoglobin such as sFv (single chain antigen binding protein), Fab1 or Fab2. The immunoglobulin could also be a "humanized" antibody, in which murine variable regions are fused to human constant regions, or in which murine complementarity-determining regions are grafted onto a human antibody structure (Wilder, R. B. et al., J. Clin. Oncol., 14:1383–1400, 1996). Unlike mouse or rabbit antibodies, "humanized" antibodies often do not undergo an undesirable reaction with the immune system of the subject. The terms "sFv" and "single chain antigen binding protein" refer to a type of a fragment of an immunoglobulin, an example of which is sFv CC49 (Larson, S. M. et al., Cancer, 80:2458–68, 1997).

Anti-heparanase antibodies are described in length in U.S. patent application Ser. No. 09/071,739, which is incorporated by reference as if fully set forth herein.

Another examples include naturally or man-made (synthetic) agents. Candidate agents for inhibiting heparanase catalytic activity include, but are not limited to, polyanionic molecules, chemically modified species of heparin, size homogeneous oligosaccharides derived from depolymerized heparin, libraries of small molecules (combinatorial library of similar agents) and rationally designed molecules for anti-heparanase catalytic activity.

According to one embodiment of the present invention evaluating the catalytic activity of the recombinant heparanase enzyme toward the heparanase substrate and the effect of the agent or agents thereupon is effected by a size separation assay adapted for detection of degradation products of the heparanase substrate. Suitable size separation assays include, bur are not limited to, gel electrophoresis and column chromatography. Other size separation methods are not excluded.

However, according to a presently preferred embodiment of the present invention, quantitatively evaluating the catalytic activity of the glycosidase or heparanase enzyme toward the glycosidase or heparanase substrate and the effect of the agent or agents thereupon is effected by an assay adapted for detection of reducing moieties associated with degradation products of the glycosidase or heparanase substrate. The assay is preferably a reducing sugar assay.

Preferably, quantitatively evaluating the catalytic activity of the glycosidase enzyme toward the glycosidase substrate and the effect of the agent or agents thereupon is effected by a calorimetric assay. A suitable colorimetric assay is the tetrazolium blue assay in which tetrazolium blue is reduced to a soluble colored formazan salt. Other quantitative colorimetric assays as, for example, described hereinabove are also envisaged.

As used herein in the specification and in the claims section below, the term "colorimetric" refers to any color producing reaction be it a simple color reaction, which is readily detectable, a fluorimetric reaction or a luminescent (e.g., chemoluminiscent) reaction, which are readily detectable by fluorescence detecting equipment.

The method preferably behaves substantially linearly in suitable ranges of enzyme concentrations and of time, such that kinetic constants of the assayed enzyme, e.g., under or without inhibition, are readily extractable.

The present invention provides novel qualitative and quantitative assays for determining glycosidase (e.g., heparanase) catalytic activity, which may therefore be used for screening potential inhibitors of glycosidases, which may serve for therapeutical purposes.

The assays are calorimetric and therefore obviate the need for size separation and for the use of radiolabeled substrates.

The qualitative assays, e.g., the carbazole assay which detects uronic acid derivatives present in complete hydrolyzates of products released from an immobilized substrate, and the dimethylmethylene blue assay, which yields color shift in the presence of polyanionic compounds, are applicable for both crude extracts as well as purified enzymes.

The quantitative assay, on the other hand, is based on the tetrazolium blue assay which calorimetrically detects reducing ends released from the substrate, which may therefore be in either soluble or immobilized form.

The quantitative assay requires pure enzyme and substrate for accuracy and linearity. This however is not a limitation when examining heparanase, for example, which following its cloning and expression is readily available in large amounts.

EXAMPLES

Reference is now made to the following examples, which together with the above descriptions, illustrate the invention in a non limiting fashion.

Materials and Experimental Methods

Materials: Sodium heparin from porcine intestinal mucosa (PM-heparin) (Mr. 14,000, Anti-FXa 165 IU/mg, sulfur content 12%) was obtained from Hepar Industries (Franklin, Ohio). A low Mr. fragment (Kabi 2165, Fragmin) of this heparin (Mr. 5,100, Anti-FXa 130 IU/mg, sulfur content 12.4%) was prepared as sodium salt by nitrous acid depolymerization (18). Heparan sulfate from bovine kidney (Cat. No. H 7640), PEG 300 (Cat. No. P 3140), tetrazolium blue chloride (Cat. No. T 4375) and carbazole (Cat. No. C 5132) were purchased from Sigma. Heparin was purchased from Welding. Heparin-sepharose was purchased from Pharmacia. 1,9-Dimethylmethylene blue was purchased from Aldrich (Cat. No. 34108).

Preparation and characterization of oligosaccharides from nitrous acid depolymerized heparins: heparin fragments consisting of saccharide chains of different sizes were obtained by partial deaminative cleavage of heparin from porcine intestinal mucosa using nitrous acid, as described (18). Sizes ranged from disaccharides to chains with an average length of the starting heparin, i.e., chains of about 40–50 saccharides. Size homogeneous oligosaccharides, similar to the starting heparin in their sulfur/carbon ratio, were prepared also by alkaline treatment of heparin methyl ester (β-elimination) as described elsewhere (19). Similar results were obtained. In both cases, the mixture of heparin fragments was subjected to ion exchange chromatography on DEAE Sepharose using sodium chloride as an eluent. Three fractions were collected: low sulfate fraction, sulfur/carbon ratio (by elemental analysis) 0.14; medium sulfate fraction, sulfur/carbon ratio 0.19; and high sulfate fraction, sulfur/carbon ratio 0.21 (19, 20). Each of the low sulfate, medium sulfate, and high sulfate fractions was further separated into size-homogenous, even-numbered oligosaccharides by gel permeation chromatography on Sephadex G-50 superfine (19, 20). This procedure resulted in a set of oligosaccharides of different sizes and degrees of sulfation. The oligosaccharides having a higher sulfur/carbon ratio than heparin were found by $^1$H-NMR and $^{13}$C-NMR spectroscopy to have their additional sulfate groups mainly in the glucosamines as indicated by a larger proportion of N-sulfate groups over N-acetyl groups and of 6-O-sulfate groups over 6-OH groups. The low sulfate-containing oligosaccharides had a considerably reduced sulfate content in their glucosamines as well as in their iduronic acids (19).

Modified heparins: Chemically modified non-anticoagulant species of heparin were prepared from native heparin and heparin fragment (Fragmin, Mr. about 5,100). Briefly, the pyridinium salt of heparin and heparin fragment underwent complete N-desulfation by incubation with dimethyl sulfoxide and methanol (21). Total desulfation of N and O sulfate groups was obtained by exhaustive desulfation with dimethyl sulfoxide containing 10% methanol and 0.4% trifluoroacefic acid. The N-desulfated heparin fragment was N-acetylated with acetic anhydride in water at pH 7–8 (20), or N-resulfated with sulfur trioxide trimethylamine complex, as described (20). An O-desulfated, N-acetylated heparin fragment was obtained by O-desulfating an N-acetylated heparin fragment, as described (20, 22). Intact heparin was chemically modified by the same procedures. These modified heparins exhibited <5% of the anticoagulant activity of heparin (23). The chemical modifications made in the heparin fragments were assessed by $^1$H NMR and $^{13}$C NMR spectroscopy using a JEOL GX-400 instrument, 400 Mhz for $^1$H and 100 MHz for $^{13}$C, and TSP (2,2,3,3-tetradeuterio-3-trimethylsilylpropionate) as an internal standard (23).

Polyanionic molecules: Compounds RG-13577 and P-97100 (polymers of 4-hydroxyphenoxy acetic acid, Mr. about 5,800) and their sulfated variant AV-1/9-1 were synthesized as described (27). Computer assisted molecular modeling suggests that these compounds form a superstructure that ensures a regular spatial distribution of negative charges, similar to that of heparin.

Cells: Cultures of bovine corneal endothelial cells were established from steer eyes as previously described (24). Stock cultures were maintained in DMEM (1 g glucose/liter) supplemented with 10% newborn calf serum, 5% fetal calf serum (FCS), 50 U/ml penicillin, and 50 µg/ml streptomycin at 37° C. in 10% $CO_2$ humidified incubators. Partially purified brain-derived βFGF (100 ng/ml) was added every other day during the phase of active cell growth (20). Highly metastatic B 16–BL6 melanoma cells were kindly provided by Dr. I. J. Fidler (University of Texas System Cancer Center, Houston, Tex., 8). Melanoma cells were maintained in culture in DMEM (4.5 g glucose/liter) supplemented with 10% FCS, L-glutamine and antibiotics.

Preparation of dishes coated with ECM: Bovine corneal endothelial cells were dissociated from stock cultures (second to fifth passage) with trypsin/EDTA solution and plated into 4-well plates at a recombinant initial density of $2 \times 10^5$ cells/ml. Cells were maintained as described above except that 5% dextran T-40 was included in the growth medium and the cells were maintained without addition of βFGF for 12 days. The subendothelial ECM was exposed by dissolving (5 min, room temperature) the cell layer with PBS containing 0.5% Triton X-100 and 20 mM $NH_4OH$, followed by four washes in PBS. The ECM remained intact, free of cellular debris and firmly attached to the entire area of the tissue culture dish (11, 20). For preparation of sulfate-labeled ECM, corneal endothelial cells were plated into 4-well plates and cultured as described above. $Na_2[^{35}S]O_4$ (540–590 mCi/mmol) was added (40 µCi/ml) 2 and 5 days after seeding and the cultures were incubated with the label without medium change (11, 20). Ten to twelve days after seeding, the cell monolayer was dissolved and the ECM exposed, as described above.

To prepare soluble sulfate labeled proteoglycans (peak I material), the ECM was digested with trypsin (25 μg/ml, 6 hours, 37° C.), the digest concentrated by reverse dialysis, applied onto a Sepharose 6B gel filtration column and the high molecular weight material (Kav<0.2, peak I) was collected (25). More than 80% of the labeled material was shown to be composed of heparan sulfate proteoglycans (11).

Degradation of sulfated proteoglycans: Sulfate labeled ECM was incubated (3 hours, 37° C., 10% $CO_2$ incubator) with intact cells, or conditioned medium at pH 6.6 and 6.2, respectively. To evaluate the occurrence of proteoglycan degradation, the incubation medium was collected and applied for gel filtration on Sepharose 6B columns (0.9×30 cm). Fractions (0.2 ml) were eluted with PBS at a flow rate of 5 ml/hours and counted for radioactivity using Bio-fluor scintillation fluid. The excluded volume (Vo) was marked by blue dextran and the total included volume (Vt) by phenol red. The latter was shown to comigrate with free sulfate (11, 20). Degradation fragments of HS side chains were eluted from Sepharose 6B at 0.5<Kav<0.8 (peak II, 11, 20). A nearly intact HSPG released from ECM by trypsin—and, to a lower extent, during incubation with PBS alone—was eluted next to Vo (Kav<0.2, peak I). Recoveries of labeled material applied on the columns ranged from 85 to 95% in different experiments. Each experiment was performed at least three times and the variation of elution positions (Kav values) did not exceed +/−15%.

Tumor metastasis: C57BL mice received a single subcutaneous (except when stated otherwise) injection of heparin (400 μg/0.2 ml/mouse, except when stated otherwise) twenty minutes prior to an intravenous inoculation of B16–BL6 melanoma cells ($1 \times 10^5$ cells/mouse). Mice were sacrificed 15 days later, the lungs fixed in Bouen's solution and scored for the number of metastatic nodules (8).

Expression of heparanase in yeast cells:

Construction of an expression vector for expression in yeast: Construction of the yeast expression vector was a multiple step process. The plasmid pFASThpa2 (described in U.S. patent application Ser. No. 09/071,618) was digested with the restriction enzymes StuI and BfrI. The large fragment isolated was ligated to a PCR amplification product generated as follows: A pair of primers MF-533 5'-ACCATATGAAAAAGTTCAAGAACAGC-3'(SEQ ID NO:1), in which nucleotides 9–26 correspond to nucleotides 534–551 in SEQ ID NO:9 disclosed in U.S. patent application Ser. No. 09/109,386, and an antisense hpa primer HPL-M1160 5'-CAGCCACATAAAGCCAGCTGC-3' (SEQ ID NO:2) which corresponds to nucleotides 1160–1140 in SEQ ID NO:9 disclosed in U.S. patent application Ser. No. 09/109,386, were used in PCR amplification of pFASThpa2. PCR conditions were: denaturation—94° C., 40 seconds; annealing—50° C., 80 seconds; and elongation—72° C., 180 seconds, total of 30 cycles. The PCR product was digested with NdeI, followed by treatment with Klenow fragment to generate blunt ended DNA fragments. The blunt product was further digested with BfrI and approximately 220 bp DNA fragment was isolated by gel electrophoresis and was thereafter ligated to the above mentioned pFASThpa2 StuI-BfrI fragment. The resulting plasmid was designated pFASThpa45. pFASThpa45 was digested with EcoRI and NotI and the insert was then ligated to the EcoRI-NotI sites of the expression vector pPIC3.5K (Invitrogen). The resulting plasmid was designated pPIC3.5K-IMhpa.

Transformation and screening: The yeast *Pichia pastoris* SMD 1168 (his3, pep4, Invitrogen) was used as a host for transformation. Transformation and selection were carried out as described in the Pichia expression kit protocol (Invitrogen). The expression vector pPIC3.5K-IMhpa was digested with SalI prior to introduction into the yeast cells.

Multiple copy clones were selected using G-418 (Boeheringer Mannehime) as follows: Following transformation, the top agar layer containing the yeast cells was removed and re-suspended in 10 ml of sterile water. Aliquots were removed and plated on YPD plates (1% yeast extract, 2% peptone, 2% glucose) containing increasing concentrations of G-418 (up to 4 mg/ml). Single colonies were picked and streaked again on YPD plates. G-418 resistance was then further confirmed by streaking again isolates on YPD-G-418 plates.

Expression experiments: Single colonies were inoculated into 5 ml buffered glycerol-complex medium (BMGY, 1% yeast extract, 2% peptone, 100 mM potassium phosphate buffer pH 6.0, 1.34% yeast nitrogen base with ammonium sulfate without amino acids, $4 \times 10^{-5}$% biotin and 1% glycerol) and incubated at 30° C. at 250 revolutions per minute (rpm) agitation for 48 hours. Cells were harvested using clinical centrifuge and re-suspended in 3 ml buffered methanol-complex medium (BMMY, the same as BMGY except that 0.5% methanol replaces the 1% glycerol). Cells were then incubated at 30° C. at 250 rpm agitation for 48 hours. Culture supernatant (induction medium) of one of the *Pichia pastoris* clones (isolated from 3 mg/ml G-418 YPD plate) was used for detection of human heparanase catalytic activity secreted from yeast.

Heparanase catalytic activity assays:

Polyacrylamide gel analysis of Heparanase catalytic activity: 6 μg heparin (Welding) or heparan sulfate (Sigma) dissolved in $H_2O$ were incubated for 6–24 hours at 37° C. with recombinant purified Heparanase (1 μg) in a 100 μl reaction mixture-buffer A containing 20 mM Phosphate citrate buffer pH 5.4, 1 mM $CaCl_2$, 1 mM NaCl and 1 mM DTT. At the end of incubation period, 0.25 volume of 5x glycerol loading buffer (80% glycerol, 5 mM CDTA) was added. The samples (50 μl) were fractionated on a 7.5% (for heparan sulfate samples) or 10% (for heparin samples) polyacrylamide mini-gel in TAC buffer (40 mM Tris, 20 mM sodium acetate, 1 mM CDTA, pH 7.8). The gel was run for 45 minutes at 100 volts and stained with 0.1% methylene blue in 50% ethanol for 10 minutes. Destaining was performed with $H_2O$. Activity was detected as a shift in the mobility of the products produced due to the enzymatic activity as compared to a non treated substrate.

Immobilized substrate: 100 μl heparin sepharose (50% suspension in 1 x buffer A) were incubated in 0.5 ml eppendorf tubes placed on a head-over-tail shaker (37° C., 17 hours) with recombinant heparanase preparations in reaction mixtures containing 20 mM phosphate citrate buffer pH 5.4, 1 mM $CaCl_2$, 1 mM NaCl and 1 mM DTT, in a final volume of 200 μl. Enzyme preparations used were either purified recombinant heparanase expressed in insect cells, crude extracts of human 293 cells expressing recombinant human heparanase, or yeast growth medium to which heparanase was secreted from cells expressing recombinant human heparanase. At the end of the incubation time, the samples were centrifuged for 5 minutes at 13,200 rpm. Following incubation, the products released to the supernatant due to the heparanase activity were analyzed using either one of the following calorimetric assays: the carbazole assay or the dimethylmethylene blue assay, as follows.

Carbazole assay: Supernatants (83 μl) were transferred into glass tubes, 420 μl sulfuric acid tetraborate (2.39 grams sodium tetraborate decahydrate in 250 ml concentrated H₂SO₄) were added, and the samples were boiled for 20 minutes. After boiling, the samples were cooled for 5 minutes on ice and 16.7 µl carbazole reagent (125 grams carbazole in 100 ml ethanol) were added to each sample. The samples were boiled for another 10 minutes. After cooling, the absorbance of the samples was determined using a spectrophotometer (CECIL CE2040) at 530 nm. To each sample a control containing a boiled enzyme was included. In each assay a standard curve containing 3–17 µg glucuronolactone was included. Heparanase activity is expressed as the amount of glucoronolactone equivalent (µg) formed per minute.

Dimethylmethylene blue assay: Supernatants (100 µl) were transferred to plastic cuvettes. The samples were diluted to 0.5 ml with PBS plus 1% BSA. 0.5 ml 1,9-Dimethylmethylene blue (32 mg dissolved in 5 ml ethanol and diluted to 1 liter with formate buffer) was added to each sample. Absorbance of the samples was determined using a spectrophotometer (CECIL CE2040) at 530 nm. To each sample a control containing a boiled enzyme was included. In each assay a standard curve containing 1–12 µg low molecular weight heparin was included. Heparanase activity is expressed as the amount of heparn (µg) formed per minute.

Heparanase catalytic activity high-through-put assay: Human recombinant heparanase expressed in insect cells was purified according to as described in U.S. patent application Ser. Nos. 09/109,386 and 09/071,618, except that DTT was not added to the elution buffer (DTT caused a high background in the Tetrazolium blue assay due to its reducing activity). Heparanase catalytic activity was determined in reactions containing 20 mM Phosphate citrate buffer pH 5.4, 1 mM CaCl₂, 1 mM NaCl, 10% PEG 300 and 50 µg heparan sulfate in a final volume of 100 µl. The reaction was performed in a 96 well microplate with 0.25–4 µg partially purified recombinant heparanase enzyme. The samples were incubated in a 37° C. incubator for 2–24 hours, on a vortex shaker. At the end of incubation, reactions were stopped by adding 100 µl Tetrazolium blue reagent (0.11% tetrazolium blue in 0.1 M NaOH) to each well. Color was developed by incubation of the plates at 60° C. for 40 minutes. Color intensity was quantitatively determined in a microplate reader (Dynatech) at 580 nm. For each assay a control reaction, not containing the substrate (heparan sulfate) was included. A glucose standard curve of 1–15 µg glucose was also included for each assay. Heparanase catalytic activity was calculated as ΔO.D of the sample containing the substrate minus the sample not containing the substrate. The background O. D. produced by the substrate was also subtracted from all the samples. The results were converted to µg glucose equivalent. One glucose unit is defined as µg glucose equivalent produced per minute. Specific activity is defined as units per mg protein.

Experimental Results

Identifying substrates for heparanase enzyme: Assessment of substrate specificity of the recombinant baculovirus derived human recombinant heparanase toward heparin and heparan sulfate was determined using a modified semi-quantitative polyacrylamide gel assay (48). Using this analysis the substrate (heparin or heparan sulfate) and the heparanase mediated degradation products are separated in a polyacrylamide gel. The gel is stained using methylene blue which reacts with the non treated substrate as well as with the heparin and heparan sulfate fragments. A substrate incubated in the absence of enzyme (control) migrates slower than the digested heparin or heparan sulfate. As shown in FIG. 1, with both heparin (lanes a and b) and heparan sulfate (lanes c and d), the degradation products migrate toward the bottom of the gel, indicating that both heparan sulfate and heparin are substrates for the human recombinant heparanase enzyme.

Figure 2A:
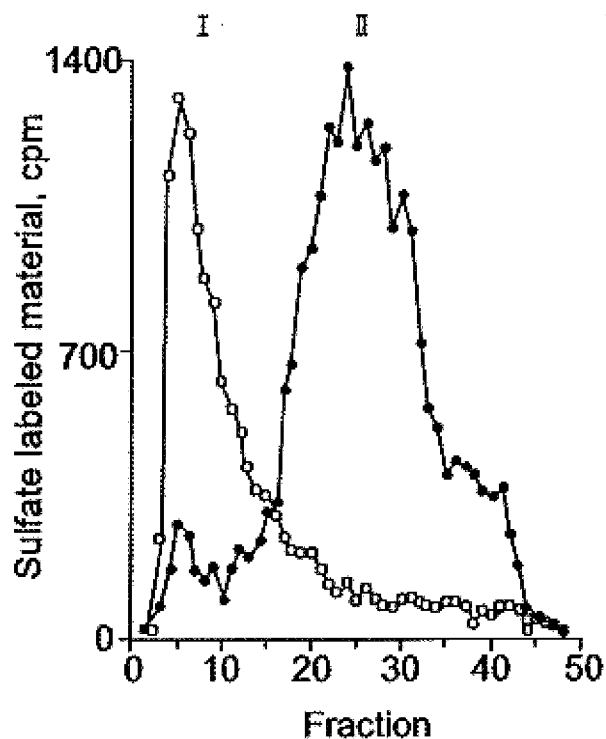
FIGS. 2a–b demonstrate apparent inhibition of heparanase catalytic activity by heparin. Recombinant heparanase was incubated (24 hours, 37° C., pH 6.6) with sulfate labeled ECM (FIG. 2a) or sulfate labeled ECM-derived soluble HSPG (peak I material, FIG. 2b, ◇), in the absence (peak II, •) and presence (peak I, □, △) of 5 μg/ml heparin. Sulfate labeled degradation products were analyzed by gel filtration over Sepharose 6B.

Effect of heparin, heparin fragment and oligosaccharides derived from depolymerized heparin on heparanase catalytic activity:

(i) intact heparin: Sulfate labeled ECM was incubated (24 hours, 37° C.) with recombinant heparanase in the absence and presence of intact heparin, an alternative substrate of the heparanase enzyme (FIG. 2a, 23). Sulfate labeled material released into the incubation medium was analyzed by gel filtration on Sepharose 6B. In the presence of the incubation medium alone, there was a constant release of labeled material that consisted almost entirely (>90%) of large Mr. fragments eluted with or next to Vo. We have previously shown that a proteolytic activity residing in the ECM itself (26) is responsible for release of the high Mr material. This nearly intact heparan sulfate proteoglycan provides a soluble substrate for subsequent degradation by heparanase, as also indicated by the relatively large amount of peak-I material accumulating when the heparanase enzyme is apparently inhibited by heparin (FIG. 2a). On the other hand, incubation of the labeled ECM with the recombinant heparanase resulted in release of 60–70% of the ECM-associated radioactivity in the form of low Mr. sulfate-labeled fragments (peak II, 0.5<Kav<0.75, FIG. 2a).

Figure 2B:
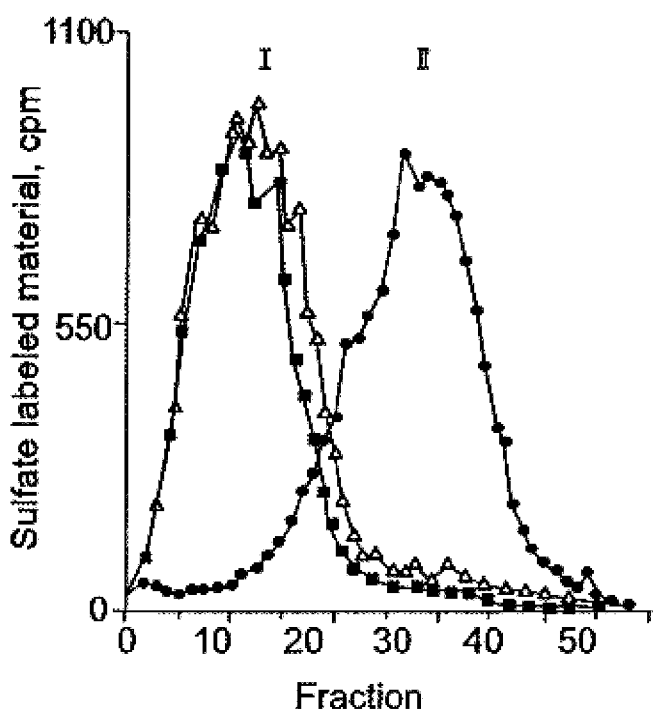
Figure 3:
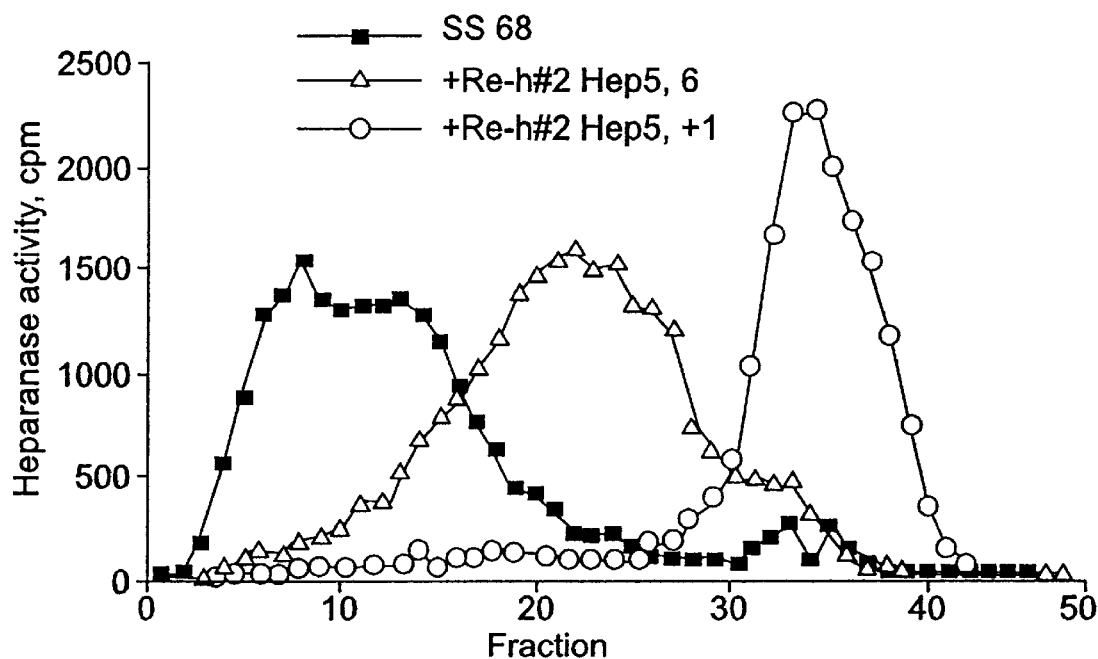
FIG. 3 demonstrates the susceptibility of Peak II material to nitrous acid deamination. Sulfate labeled ECM-derived soluble HSPG (peak I material) was incubated (37° C., 2 hours, pH 6.2) with recombinant heparanase in a total volume of 1 ml. The reaction mixture (0.5 ml) was subjected to nitrous acid deamination (0.24 M $NaNO_3$ in 1.8 M acetic acid, 80 minutes, 24° C.). The substrate (■; SS 68), untreated (△; +Re-h#2 Hep5, 60'), and nitrous acid treated (○+Re-h#2 Hep5+N.Acid) peak II material were subjected to gel filtration over Sepharose 6B columns.

In a similar experiment, soluble sulfate labeled peak I material (nearly intact ECM-derived heparan sulfate proteoglycans) was incubated with recombinant heparanase in the absence and presence of heparin (FIG. 2b). We refer below to heparin and other compounds as heparanase inhibitors, although some or all of which, such as heparin, may be heparanase substrates. Conversion of the radiolabeled high molecular weight peak I substrate into low molecular weight peak II material was completely inhibited, in the presence of 1 µg/ml heparin, (FIG. 2b). This effect is probably due to the excess of the non-labeled substrate (heparin) since the addition of substrate in excess may interfere with heparanase endogenic substrates. Degradation fragments eluted in peak II were shown to be degradation products of heparan sulfate, as they were (i) 5 to 6 fold smaller than intact heparan sulfate side chains (Kav about 0.33) released from ECM by treatment with either alkaline borohydride or papain; and (ii) resistant to further digestion with papain or chondroitinase ABC (not shown) and susceptible to deamination by nitrous acid (FIG. 3).

Figure 4:
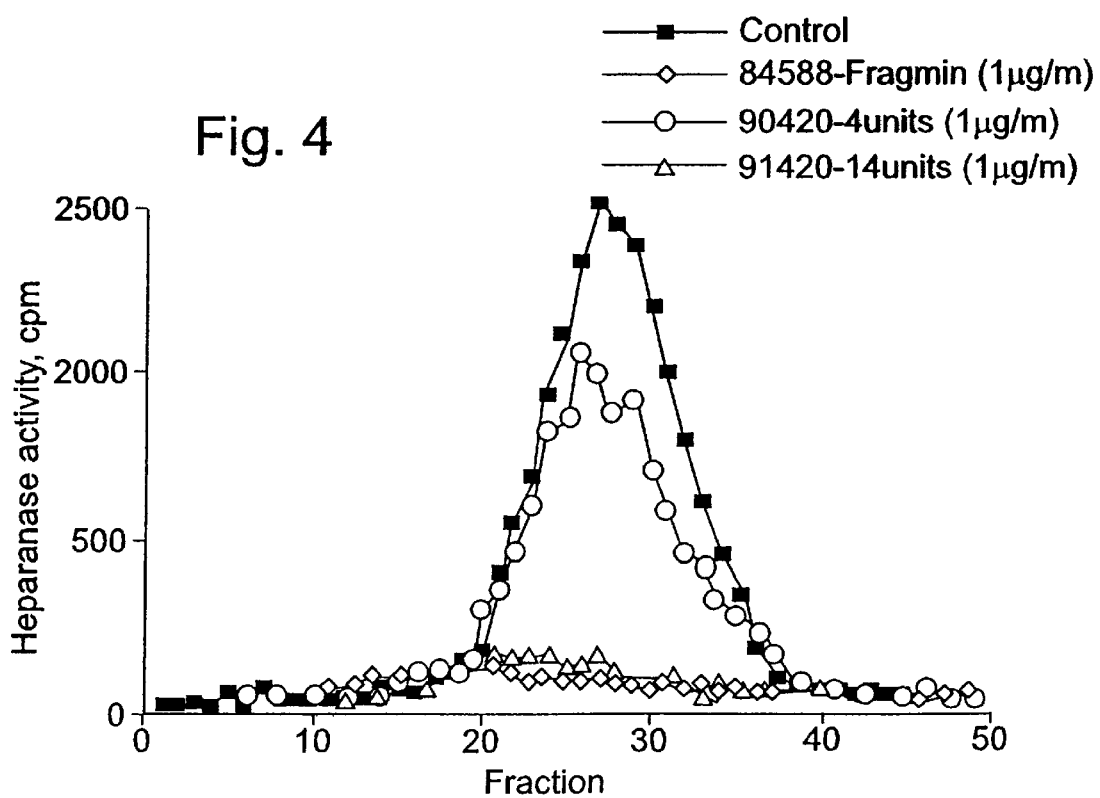
FIG. 4 demonstrates inhibition of heparanase by heparin derived oligosaccharides of varying sizes. Sulfate labeled ECM was incubated (37° C., 24 hours, pH 6.2) with recombinant heparanase in the absence (control) and presence of 1 μg/ml heparin fragment (84588-Fragmin) or size homogenous tetra and tetradeca-saccharides (90420-4 units and 19420-14 units, respectively) prepared by nitrous acid depolymerization of heparin. Sulfate labeled material released into the incubation medium was analyzed by gel filtration over Sepharose 6B columns.

(ii) heparin-derived oligosaccharides: We investigated the inhibitory effect of size homogenous oligosaccharides containing 4 and 14 sugar units, prepared from heparin by nitrous acid depolymerization (FIG. 4). As demonstrated in FIG. 4, complete inhibition of recombinant heparanase was observed in the presence of 1 µg/ml of the tetradecasaccharide (91420–14 units). A similar result was observed with heparin derived oligosaccharides containing 16 and 18 sugar units (not shown), while there was a very slight inhibition by 1 µg/ml of the tetrasaccharide (90420–4 units). Similar results were obtained with oligosaccharides derived from heparin by nitrous acid depolymerization (FIG. 4, 84588-Fragmin) or by alkaline β-elimination (not shown).

Figure 5:
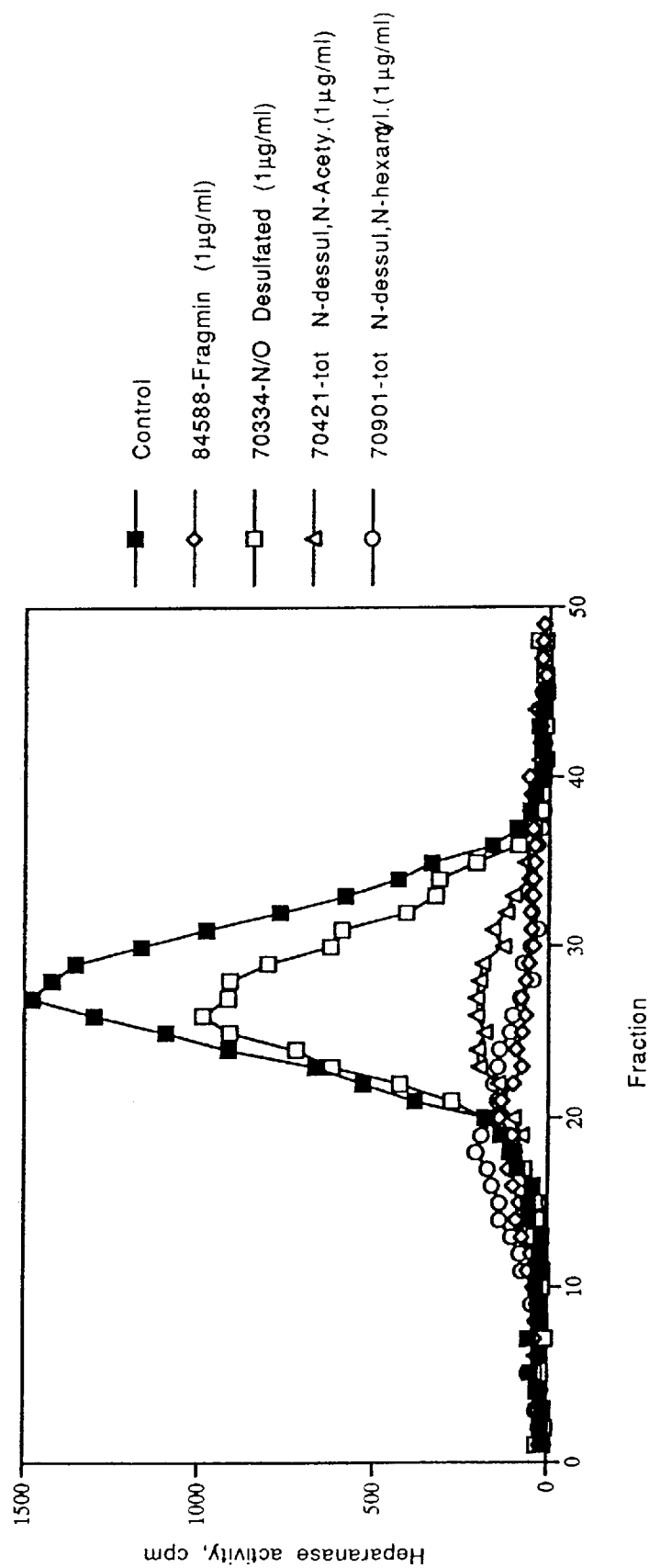
FIG. 5 demonstrates inhibition of heparanase by chemically modified species of heparin fragment. Sulfate labeled ECM was incubated (37° C., 24 hours, pH 6.2) with recombinant heparanase in the absence (control) or presence of 1 μg/ml heparin fragment (84588-Fragmin), totally desulfated (N-, O-) heparin fragment (70334-N/O) and species of heparin fragment in which the N-sulfates were substituted with acetyl (70421, N-acetyl) or hexanoyl (70901, N-hexanoyl) groups. Sulfate labeled material released into the incubation medium was analyzed by gel filtration over Sepharose 6B.

(iii) Chemically modified species of heparin: Chemically modified non-anticoagulant species of heparin fragment (low molecular weight heparin, Fragmin, Mr. of about 5,100,), prepared as described under Experimental Methods, were incubated with sulfate labeled ECM in the absence and presence of heparin fragment (84588-Fragmin), N/O totally desulfated heparin fragment (sulfate<1%, 70334-N/O desulfated), and either N-acetylated (70421-tot) or N-hexanoylated (70901-tot) heparin fragments. Accumulation in the medium of low Mr. sulfate labeled degradation fragments was completely inhibited in the presence of 1 µg/ml heparin fragment, but there was only a slight inhibition by 10 µg/ml N/O desulfated heparin fragment (FIG. 5). There was no inhibition of heparanase catalytic activity by 1 µg/ml of N-desulfated (sulfate equals 9.7%), or N/O-desulfated, N-resulfated (sulfate equals 5.3%) species of heparin (not shown), indicating that both the N- and O-sulfates of heparin are required for inhibition of recombinant heparanase. Substitution of the N-sulfates of heparin fragment with acetyl or hexanoyl groups (sulfate equals 8.7% and 7.5%, respectively) yielded species of heparin which inhibited heparanase catalytic activity nearly as well as heparin fragment (FIG. 5; i.e., complete inhibition in the presence of 1 µg/ml).

Our screening experiments using the recombinant heparanase enzyme indicated that while O-desulfation abolished the heparanase inhibiting effect of heparin, O-sulfated and N-substituted (e.g., N-acetyl or N-hexanoyl) species of heparin retained a high inhibitory activity. Inhibition of recombinant heparanase was best achieved by heparin species containing 16 sugar units or more and having sulfate groups at both the N and O positions. Low sulfate oligosaccharides were less effective heparanase inhibitors than medium and high sulfate fractions of the same size saccharide. Heparin fractions with high and low affinity to antithrombin III exhibited a similar high heparanase inhibitory activity, despite a 200 fold difference in their anti-coagulant activity (not shown).

(iv) Synthetic polyanionic heparin-mimicking compounds: heparin and heparan sulfate (HS) participate in the regulation of many cellular processes, particularly as they relate to cell growth and differentiation, tumor metastasis and angiogenesis, autoimmunity, lipoprotein metabolism, and gene expression, although its mode of action has not been clearly elucidated (2). Compounds that modulate functional properties of heparin and/or HS are therefore of increasing importance for the development of therapeutic agents of widespread utility. In collaboration with Rhone-Poulenc Rorer Co., we have synthesized potent mimetics of heparin/HS and investigated their mode of action and possible application in the inhibition of restenosis, angiogenesis and tumor progression (27–31). For this purpose, we applied the acid-catalyzed polymerization of phenols and formaldehyde to synthesize negatively charged, non-sulfated polyanionic compounds (27, U.S. Pat. No. 5,674,482, which is incorporated by reference as if fully set forth herein). Aromatic ring monomers were chosen and strong oxidizing reagents avoided so that the polymerization process with formaldehyde would yield substantially ordered and defined backbones. Using this approach, a series of non-toxic linear polyanionic polymers was identified with repeating phenol-based monomers, including poly-4-hydroxyphenoxy acetic acid, hereby termed compound RG-13577, that mimics some of the effects of heparin. Of particular significance is the ability of these compounds to inhibit cell proliferation (e.g., vascular endothelial and smooth muscle cells, mesangial cells, 28–30), and revert the transformed phenotype of basic fibroblast growth factor (βFGF) transfected cells (31).

With respect to the detailed chemical structure, there are several differences between RG-13577 and heparin. While heparin contains sulfonate as a major anionic group, RG-13577 contains only carboxylic residues. In addition, RG-13577 is composed of aromatic rings linked by an enzyme resistant methylene group, while heparin has a biodegradable sugar backbone. RG-13577 and heparin represent, each, a family of polymers of repeating units. The estimated molecular weight of the active compound of RG-13577 is around 8,000, while the molecular weight of commercially available heparin is within the range of 5,000–30,000. Recently, two polyanionic compounds were synthesized by InSight Ltd., Israel. One, termed P-97100, is identical to compound RG-13577 and the second is a sulfated version of compound P-97100, in which the carboxyl groups are replaced with sulfated groups. Using the recombinant heparanase enzyme and the above described assay systems, we have screened the ability of these compounds to inhibit heparanase catalytic activity.

Figure 6A:
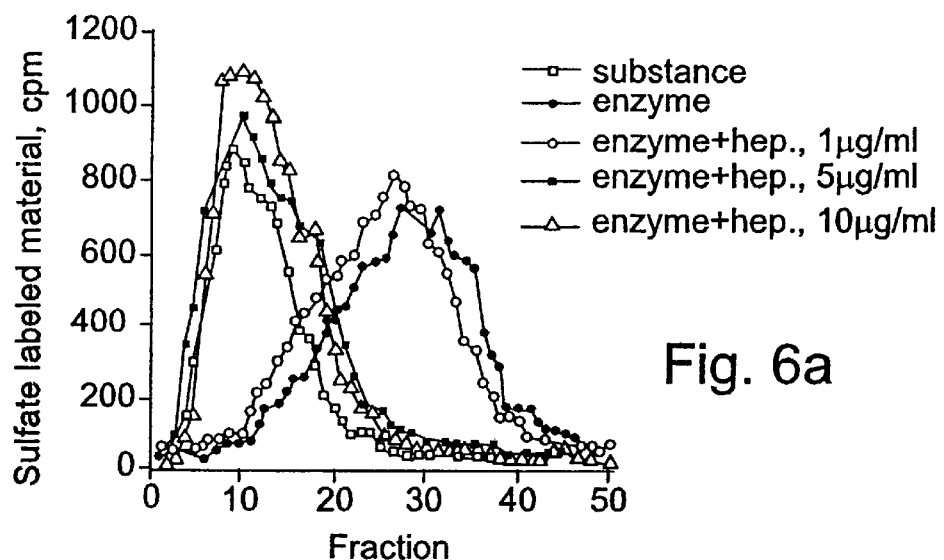
FIGS. 6a–c demonstrate inhibition of heparanase by synthetic polyanionic heparin-mimicking compounds. Sulfate labeled ECM-derived soluble HSPG (peak I material, ■) was incubated (37° C., 24 hours, pH 6.2) with recombinant heparanase in the absence (•) or presence of 1, 5, or 10 μg/ml heparin (FIG. 6a); compound P-97100 (FIG. 6b); or compound RG-13577 (FIG. 6c, ○; ■; D, respectively). Sulfate labeled degradation products were analyzed by gel filtration over Sepharose 6B.
Figure 6B:
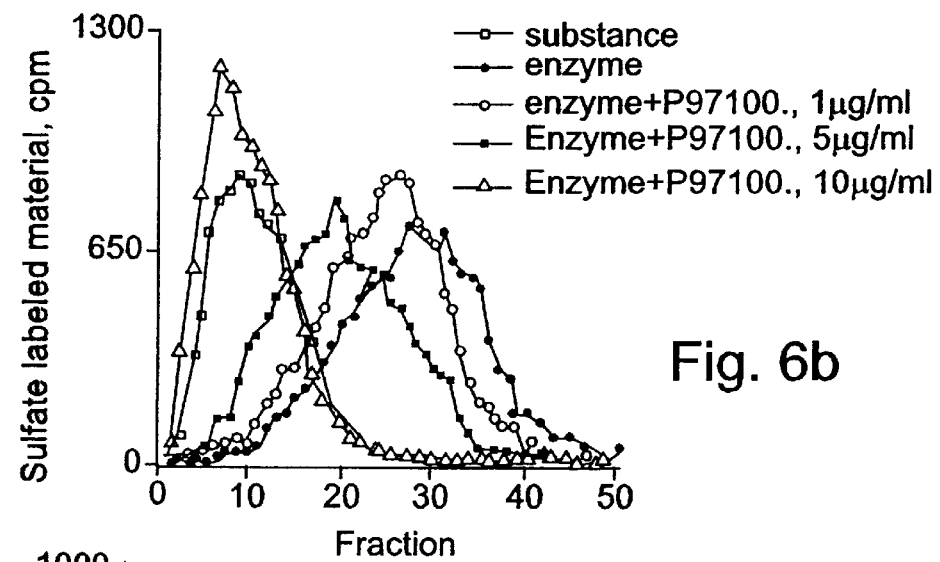
Figure 6C:
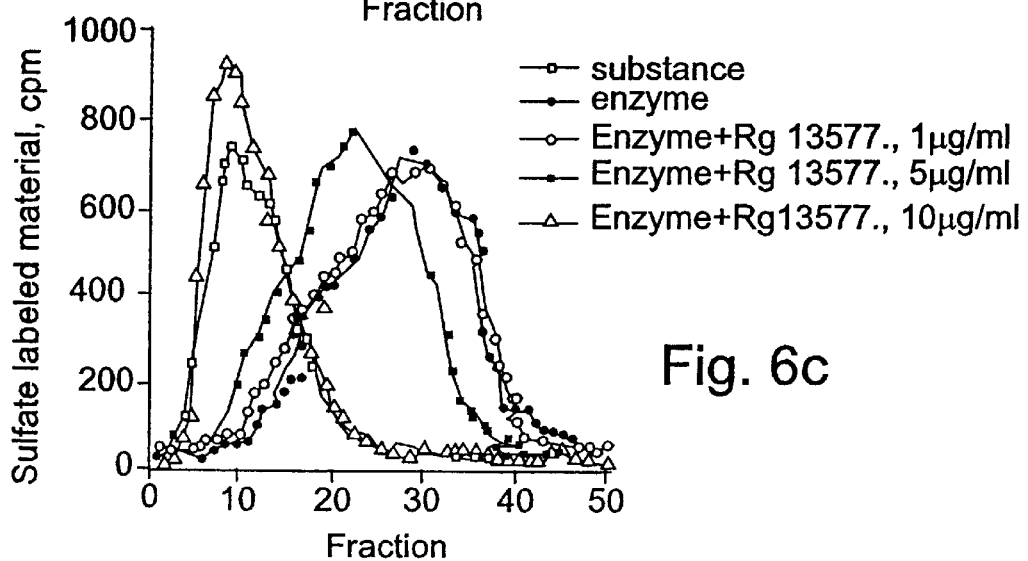

Soluble, sulfate-labeled ECM-derived HSPG substrate (peak I material) was incubated with purified recombinant heparanase in the absence and presence of increasing concentrations (1, 5 and 10 µg/ml) of heparin (FIG. 6a), compound P-97100 (poly-4-hydroxyphenoxy acetic acid, synthesized by InSight, FIG. 6b), or compound RG-13577 (poly-4-hydroxyphenoxy acetic acid, synthesized by RhOne-Poulenc Rorer, FIG. 6c). Following 18 hours incubation (37° C., pH 5.8), the reaction mixtures were subjected to gel filtration over Sepharose 6B and analyzed for conversion of the peak I substrate into low molecular weight degradation fragments. Complete inhibition of this conversion (heparanase catalytic activity) was obtained in the presence of 5 µg/ml heparin (FIG. 6a) or 10 µg/ml complete inhibition of this conversion (heparanase catalytic activity) was obtained in the presence of 5 µg/ml heparin or 10 µg/ml of each of the other compounds (FIGS. 6b–c). Heparin and compound P-97100 exerted a small inhibitory effect already at 1 µg/ml (FIGS. 6a–b), while there was no effect to RG-13577 at this concentration (FIG. 6c). It appears that in this assay system, compound P-97100 prepared by InSight was slightly more effective than RG-13577 and nearly as active as heparin.

Figure 7A:
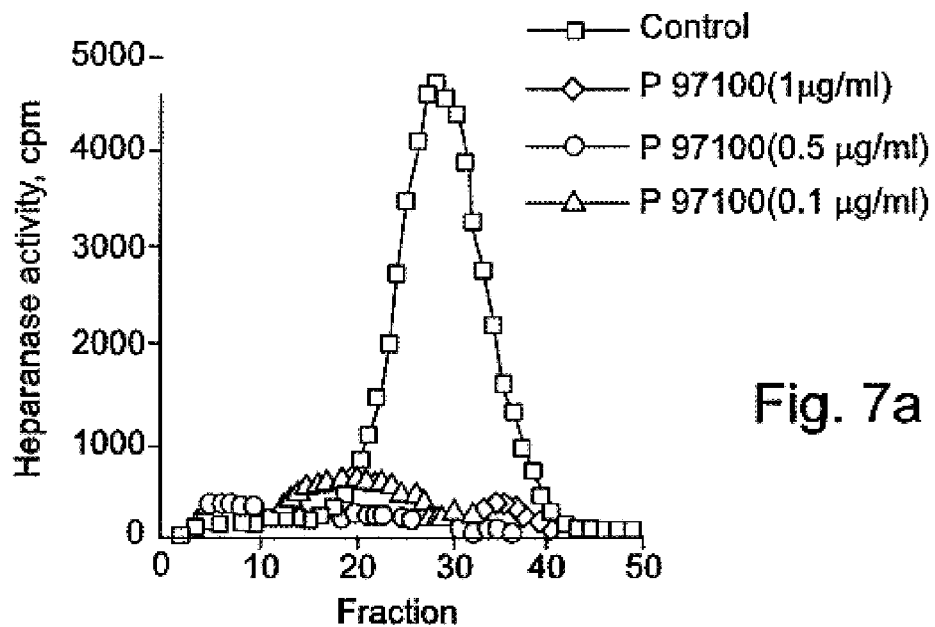
FIGS. 7a–b demonstrate inhibition of heparanase by non-sulfated and sulfated heparin-mimicking compounds. Sulfate labeled ECM-derived soluble HSPG (peak I material) was incubated (37° C., 24 hours, pH 6.2) with recombinant heparanase in the absence (control) or presence of 0.1, 0.5, or 1 μg/ml compound P-97100 (FIG. 7a); or compound AV-1/9-1 (FIG. 7b). Sulfate labeled degradation products were analyzed by gel filtration over Sepharose 6B.
Figure 7B:
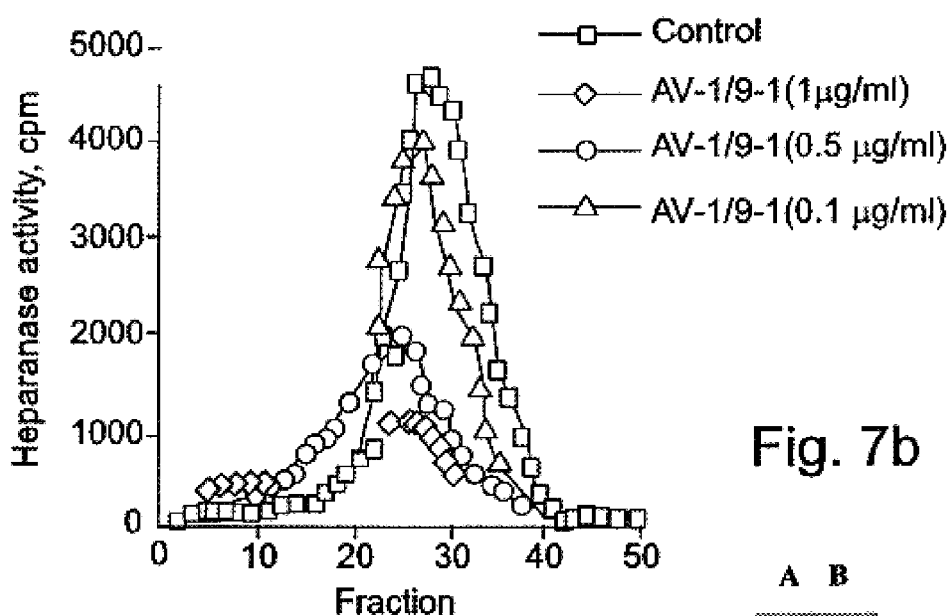
Figure 6:
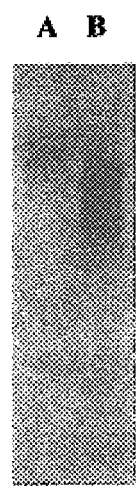

Intact, sulfate labeled ECM was applied to compare the heparanase inhibiting activity of compound AV-1/9-1 versus compound P-97100. As demonstrated in FIG. 7a, complete inhibition of recombinant heparanase catalytic activity was obtained in the presence of 0.5 and 1 µg/ml compound P-97100. An almost complete inhibition was obtained at 0.1 µg/ml compound P-97100. Under the same conditions, compound AV-1/9-1 (sulfated poly-4-hydroxyphenoxy acetic acid, synthesized by InSight) yielded a partial inhibition at 0.5 and 1 µg/ml, but there was no inhibition at 0.1 µg/ml AV-1/9-1 (FIG. 7b). These results indicate that compound P-97100 is a more potent inhibitor of heparanase catalytic activity as compared to its sulfated analog AV-1/9-1 and that the recombinant heparanase enzyme can be applied for screening purposes and detection of even small differences between potential heparanase inhibiting compounds.

Heparanase catalytic activity using an immobilized substrate: To determine whether the recombinant heparanase could utilize an immobilized substrate, a reaction was performed with heparin-sepharose as a substrate and the products of the reaction were observed using a polyacrylamide gel assay. As shown in FIG. 8, a shift in the mobility of the products of the enzymatic reaction can be detected, indicating that the recombinant heparanase can cleave an immobilized substrate.

In an attempt to develop an assay which may quantify the reaction products using crude or purified heparanase, a similar incubation of the enzyme with heparin-sepharose was made, but the products were analyzed using a colorimetric method, either the carbazole assay, which allows estimation of uronic acids, such as iduronic acids, of heparin and heparan sulfate or lactone forms of uronic acid, such as glucoronolactone (43), or the dimethylmethylene blue assay, which allows estimation of sulfated glycosaminoglycans (51).

Figure 9A:
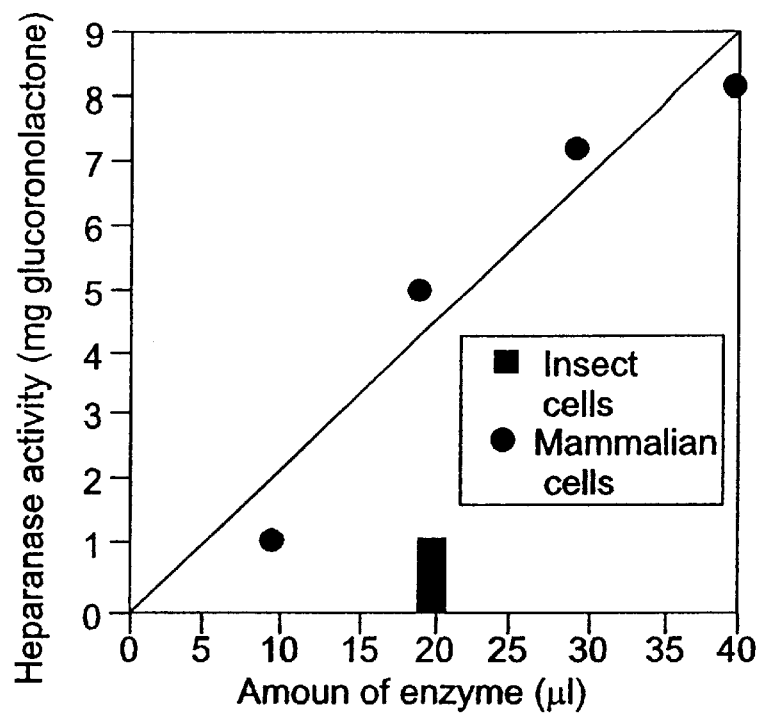
FIGS. 9a–b demonstrate determination of recombinant heparanase catalytic activity expressed by insect cells, yeast cells and mammalian cells, using the immobilized heparin and the carbazole or the dimethylmethylene blue colorimetric assays. Heparin-sepharose was incubated (37° C., 17 hours, pH 5.4) with increasing amounts of extracts of mammalian cell expressing human heparanase (•) or 20 μl (0.5 μg) of partially purified recombinant heparanase expressed in insect cells (displayed as a bar). Reaction products were analyzed using carbazole assay. Results are expressed in ng glocoronolactone equivalent units per minute (FIG. 9a). Heparin sepharose was incubated (37° C., 17 hours, pH 5.4) with increasing amounts of partially purified recombinant heparanase expressed in insect cells (0.5–1.5 μg) (•) or an enzyme secreted from transformed yeast cells (displayed as a bar). Reaction products were analyzed using the dimethylmethylene blue assay (FIG. 9b). Results are expressed in ng heparin per minute.
Figure 9B:
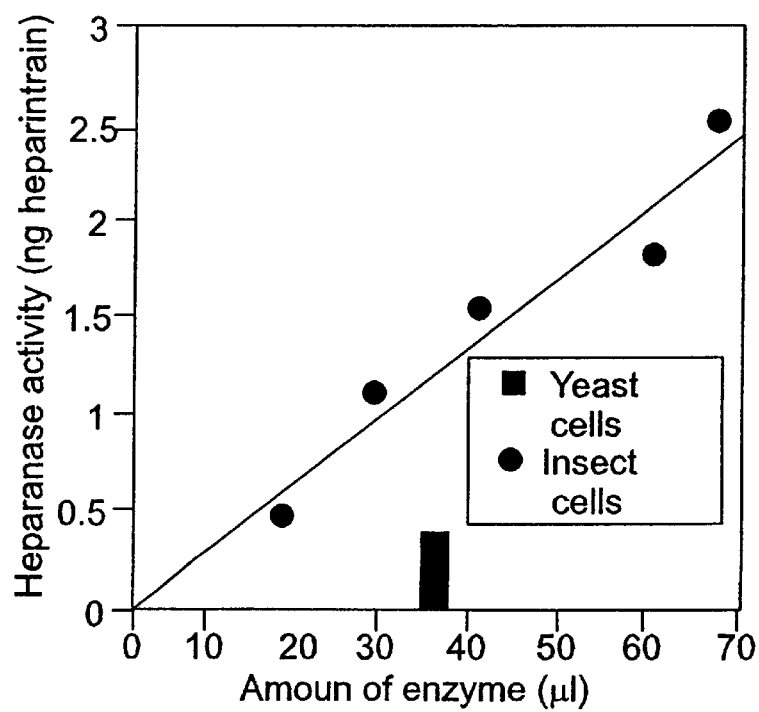

As shown in FIG. 9a, recombinant Heparanase catalytic activity expressed in either mammalian or insect cells could be quantitatively detected using the carbazole assay. The activity was found to be about 6 fold higher in the heparanase expressed in mammalian cells, although a crude preparation was used for the mammalian cells whereas the enzyme expressed in insect cells was partially purified. Similarly, as shown in FIG. 9b, products of heparanase activity, expressed in either yeast cells or insect cells, could be detected using the dimethylmethylene blue assay (FIG. 9b). The activity per µl is higher for the enzyme expressed in insect cells but the amount of heparanase expressed in yeast is much lower. From yeast, a preparation of induction medium (to which heparanase was secreted) was tested, whereas a purified enzyme was used for the enzyme expressed in insect cells.

Figure 10:
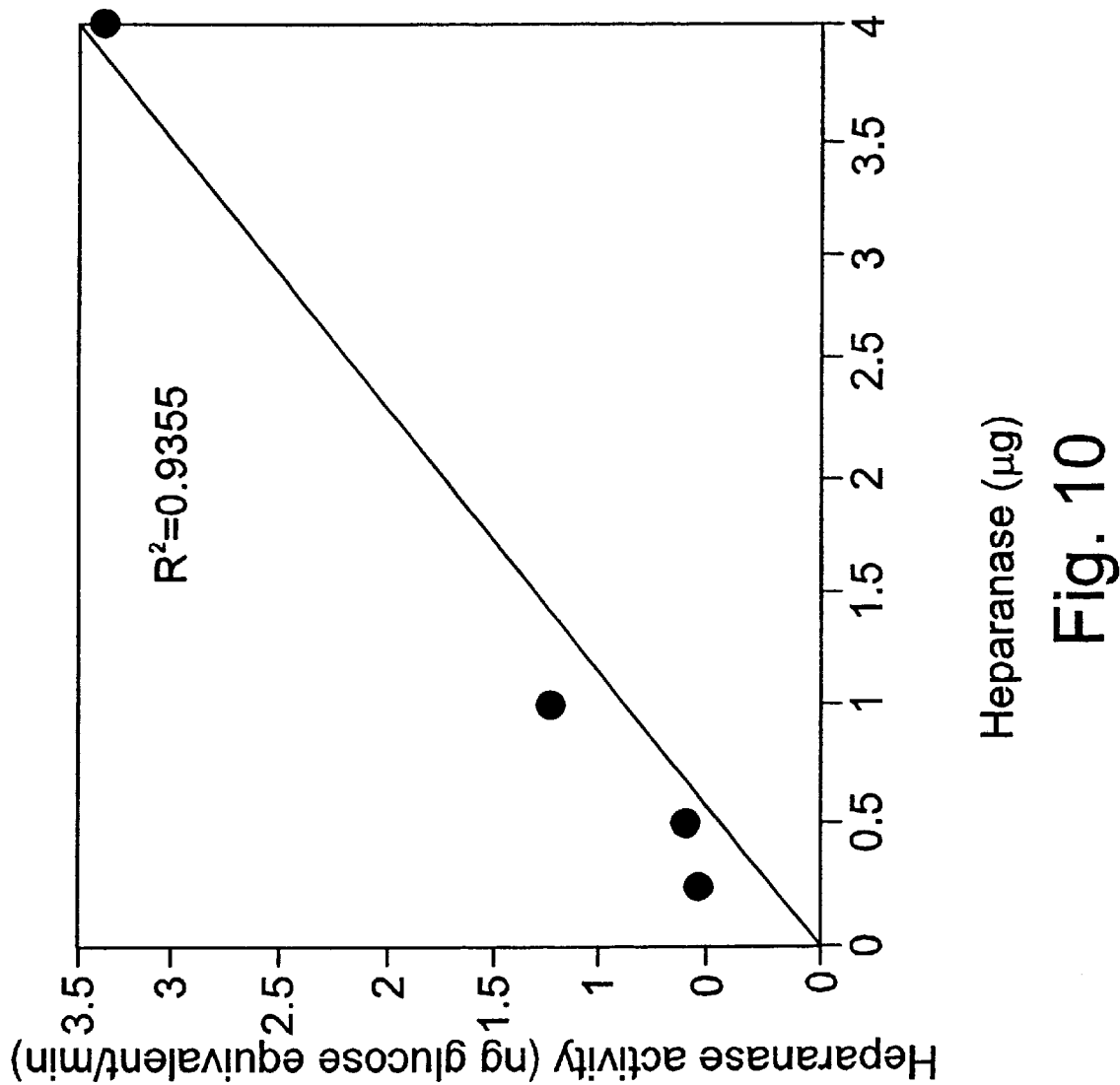
FIG. 10 demonstrates heparanase catalytic activity as a function of the amount of enzyme, using the colorimetric tetrazolium blue assay. Heparan sulfate was incubated (37° C., 6 hours, pH 5.4) with increasing amounts (0.25–4 μg) of a partially purified heparanase expressed in insect cells. Products of the enzymatic activity were quantified using the tetrazolium blue assay. The results are expressed in ng glucose equivalent units per minute. Each data point represents an average of three independent reactions.

High throughput heparanase catalytic activity assay for screening for potential anti-metastatic and anti-inflammatory agents using recombinant mammalian heparanase as a probe: Before studying the potential at the novel assay to be used for screening of potential inhibitors, it was necessary to demonstrate that the assay has linear ranges on a soluble substrate with increasing amounts of enzyme and incubation times. Recombinant heparanase, expressed in insect cells and partially purified, was used for determination of activity. PEG 300 was added to the reaction mixture to stabilize the enzyme. Increasing amounts of enzyme, 0.25–4 µg heparanase, were added to the reaction mixture and incubation was made for 6 hours at 37° C. As shown in FIG. 10, the activity of heparanase was linear with increasing amounts of enzyme, from 0.25–4 µg protein.

Figure 11:
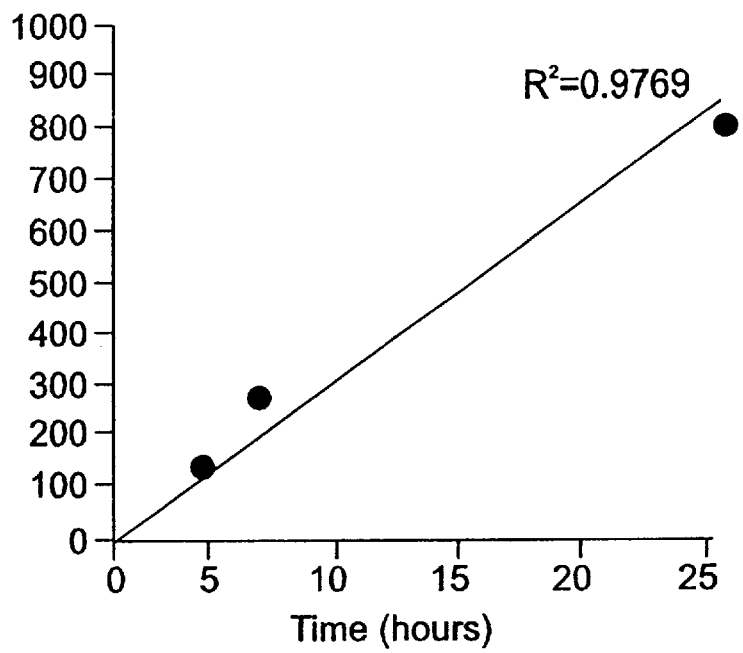
FIG. 11 demonstrates heparanase catalytic activity as a function of incubation time, using the tetrazolium blue assay. Heparan sulfate was incubated (37° C., pH 5.4) with 3 μg partially purified recombinant heparanase expressed in insect cells for increasing incubation periods (2, 4, 6, 24 hours.). Products of the enzymatic activity were quantified using the tetrazolium blue assay. The results are expressed in μg glucose equivalent (GE) per mg protein. Each data point represents an average of three independent reactions.

Next, the linearity of the activity with respect to time was examined. Reactions were incubated for 2, 4, 6 and 24 hours with 3 µg of enzyme in each reaction. As shown in FIG. 11, the activity was linear for up to 24 hours.

Figure 12:
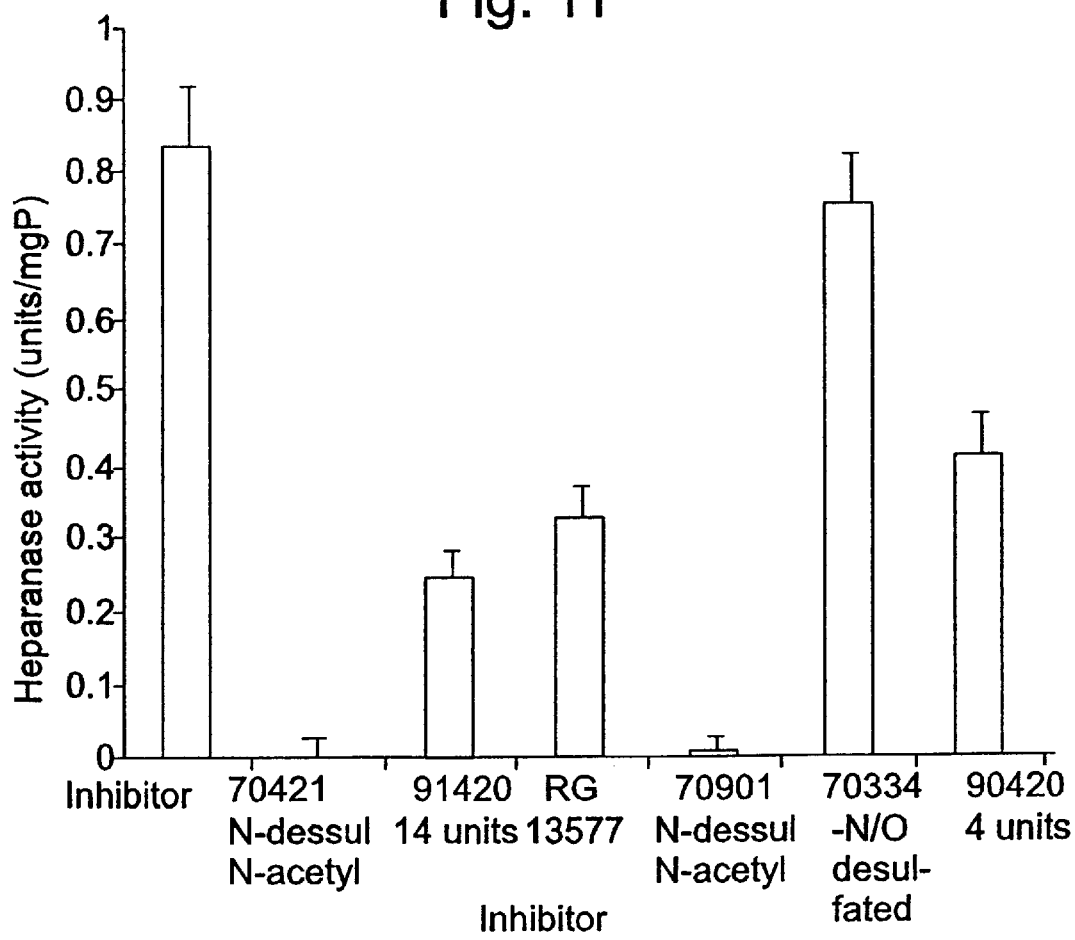
FIG. 12 demonstrate screening different potential heparanase inhibitors using the tetrazolium blue assay. Heparan sulfate was incubated (37° C., 17h, pH 5.4) with 3 μg recombinant heparanase in the absence (-inhibitor) or presence of 10 μg/ml potential inhibitor (as indicated in the Figure). The reaction products were analyzed using the tetrazolium blue assay. The activity was calculated as ΔO.D of the reaction including the substrate heparan sulfate, the enzyme and the potential inhibitor minus the same reaction but lacking the substrate. The O. D. contributed by the substrate heparan sulfate was also subtracted. The results are expressed as specific activity in glucose equivalent units per milligram protein. Each data point represents an average of three independent reactions.

In order to determine whether this assay is suitable for screening for heparanase inhibitors, several different species of heparin (chemically modified) and heparin-mimicking compounds were tested for their inhibitory effect on heparanase catalytic activity, using the recombinant enzyme and the new assay system. One or 10 µg/ml of each potential inhibitor was added to a reaction including or lacking the substrate heparan sulfate. Each reaction contained 3 µg of enzyme and was incubated for 17 hours at 37° C. The reactions in which the potential inhibitor was included were compared to a reaction not containing the compound. The background caused due to the substrate was subtracted from all activity results. The results of the effect of the different potential inhibitors at a concentration of 10 µg/ml are presented in FIG. 12. In general, the results of the inhibition of heparanase using this assay correlate well with the results obtained with labeled ECM. Compounds 70421-N-desulfated, N-acetylated Fragmin, 70901-N-desulfated, and N-hexanoylated Fragmin completely inhibited heparanase catalytic activity, while compound 70334-N/O desulfated Fragmin did not cause significant inhibition. The synthetic polyanionic heparin-mimetic, RG-13577 (25) partially inhibited heparanase catalytic activity.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

REFERENCES CITED

1. Wight, T. N., Kinsella, M. G., and Qwarnstromn, E. E. (1992). The role of proteoglycans in cell adhesion, migration and proliferation. Curr. Opin. Cell Biol., 4,793–801.

2. Jackson, R. L., Busch, S. J., and Cardin, A. L. (1991). Glycosaminoglycans: Molecular properties, protein interactions and role in physiological processes. Physiol. Rev., 71, 481–539.

3. Wight, T. N. (1989). Cell biology of arterial proteoglycans. Arteriosclerosis, 9, 1–20.

4. Kjellen, L., and Lindahl, U. (1991). Proteoglycans: structures and interactions. Annu. Rev. Biochem., 60, 443–475.

5. Ruoslahti, E., and Yamaguchi, Y. (1991). Proteoglycans as modulators of growth factor activities. Cell, 64, 867–869.

6. Vlodavsky, I., Bar-Shavit, R., Korner, G., and Fuks, Z. (1993). Extracellular matrix-bound growth factors, enzymes and plasma proteins. In Basement membranes: Cellular and molecular aspects (eds. D. H. Rohrbach and R. Timpl), pp 327–343. Academic press Inc., Orlando, Fla.

7. Vlodavsky, I., Eldor, A., Haimovitz-Friedman, A., Matzner, Y., Ishai-Michaeli, R., Levi, E., Bashkin, P., Lider, O., Naparstek, Y., Cohen, I. R., and Fuks, Z. (1992). Expression of heparanase by platelets and circulating cells of the immune system: Possible involvement in diapedesis and extravasation. Invasion & Metastasis, 12, 112–127.

8. Vlodavsky, I., Mohsen, M., Lider, O., Ishai-Michaeli, R., Ekre, H.-P., Svahn, C. M., Vigoda, M., and Peretz, T. (1995). Inhibition of tumor metastasis by heparanase inhibiting species of heparin. Invasion & Metastasis, 14: 290–302.

9. Nakajima, M., Irimura, T., and Nicolson, G. L. (1988). Heparanase and tumor metastasis. J. Cell. Biochem., 36, 157–167.

10. Liotta, L. A., Rao, C. N., and Barsky, S. H. (1983). Tumor invasion and the extracellular matrix. Lab. Invest., 49, 639–649.

11. Vlodavsky, I., Fuks, Z., Bar-Ner, M., Ariav, Y., and Schirrmacher, V. (1983). Lymphoma cell mediated degradation of sulfated proteoglycans in the subendothelial extracellular matrix: Relationship to tumor cell metastasis. Cancer Res., 43, 2704–2711.

12. Vlodavsky, I., Ishai-Michaeli, R., Bar-Ner, M., Fridman, R., Horowitz, A. T., Fuks, Z. and Biran, S. Involvement of heparanase in tumor metastasis and angiogenesis. Is. J. Med. 24:464–470, 1988.

13. Parish, C. R., Coombe, D. R., Jakobsen, K. B., and Underwood, P. A. (1987). Evidence that sulfated polysaccharides inhibit tumor metastasis by blocking tumor cell-derived heparanase. Int. J. Cancer, 40, 511–517.

14. Vlodavsky, I., Liu, G. M., and Gospodarowicz, D. (1980). Morphological appearance, growth behavior and migratory activity of human tumor cells maintained on extracellular matrix vs. plastic. Cell, 19, 607–616.

15. Vlodavsky, I., Bar-Shavit, R., Ishai-Michaeli, R., Bashkin, P., and Fuks, Z. (1991). Extracellular sequestration and release of fibroblast growth factor: a regulatory mechanism? Trends Biochem. Sci., 16, 268–271.

16. Campbell, K. H., Rennick, R. E., Kalevich, S. G., and Campbell, G. R. (1992) Exp. Cell Res. 200,156–167.

17. Lider, O., Baharav, E., Mekori, Y., Miller, T., Naparstek, Y., Vlodavsky, I. and Cohen, I. R. Suppression of experimental autoimmune diseases and prolongation of allograft survival by treatment of animals with heparinoid inhibitors of T lymphocyte heparanase. J. Clin. Invest. 83:752–756, 1989.

18. Thunberg L, Backstrom G, Grundberg H, Risenfield J, Lindahl U: Themolecular size of the antithrombin-binding sequence in heparin. FEBS Lett 1980; 117:203–206.

19. Sudhalter J, Folkman J, Svahn C-M, Bergendal K, D'Amore PA: Importance of size, sulfation and anticoagulant activity in the potentiation of acidic fibroblast growth factor by heparin. J Biol Chem 1989; 264:6892–6897.

20. Ishai-Michaeli R, Svahn C M, Chajek-Shaul T, Korner G, Ekre H P, Vlodavsky I: Importance of size and sulfation of heparin in release of βFGF from the vascular endothelium and extracellular matrix. Biochemistry 1992; 31:2080–2088.

21. Inoue Y, Nagasawa, K: Selective N-desulfation of heparin with dimethyl sulfoxide containing water or methanol. Carbohydr Res 1976; 46:87–95.

22. Nagasawa K, Inoue Y, Kamata T: Solvolytic desulfation of glycosaminoglycuronan sulfates with dimethyl sulfoxide containing water or methanol. Carbohydr Res 1977; 58: 47–55.

23. Bar-Ner M, Eldor A, Wasserman L, Matzner Y, Vlodavsky I: Inhibition of heparanase mediated degradation of extracellular matrix heparan sulfate by modified and non-anticoagulant heparin species. Blood 1987; 70:551–557.

24. Gospodarowicz D, Mescher A L, Birdwell C R: Stimulation of corneal endothelial cell proliferation in vitro by fibroblast and epidermal growth factors. Exp Eye Res 1977; 25:75–89.

25. Haimovitz-Friedman, A., Falcone, D. J., Eldor, A., Schirrmacher, V., Vlodavsky, I., and Fuks, Z. Activation of platelet heparitinase by tumor cell derived factors. Blood, 78:789–796, 1991.

26. Vlodavsky I, Komer G, Ishai-Michaeli R, Bashkin P, Bar-Shavit R, Fuks Z: Extracellular matrix-resident growth factors and enzymes: possible involvement in tumor metastasis and angiogenesis. Cancer Met Rev 1990; 9:203–226.

27. Regan J, Ben-Sasson S A, Sabatino R, Eilat D, Bruno JG, D'Alisa R, Chang MN: Mimicry of biological macromolecules by polyaromatic anionic compounds. J Bioact Compat Polymer 8:317–337, 1993.

28. Benezra M, Ben Sasson A S, Regan J, Chang M, Bar Shavit R, Vlodavsky I: Antiproliferative activity to vascular smooth muscle cells and receptor binding of heparin-mimicking polyaromatic anionic compounds. Arterioscler Thromb 14:1992–9, 1994.

29. Katz, A., Vlodavsky, I., Davies, M., Miao, H-Q., Ben-Sasson, S. A., Darmon, D., Hurwitz, H., Borgel, H., M. Benezra, M. Antiproliferative activity to glomerular mesangial cells and receptor binding of a heparin-mimicking polyaromatic anionic compound. J. Am. Soc. Nep. 8:1688–1697, 1977.

30. Miao, H-Q., Ornitz, D. M., Eingorn, E., Ben-Sasson, S. A., and Vlodavsky I. Modulation of fibroblast growth factor-2 receptor binding, dimerization, signaling and angiogenic activity by a synthetic heparin-mimicking polyanionic compound. J. Clin. Invest. 99: 1565–1575, 1997.

31. Benezra M, Vlodavsky I, YayoA, Bar Shavit R, Regan J, Chang M, Ben Sasson A S: Reversal of basic fibroblast growth factor-mediated autocrine cell transformation by aromatic anionic compounds. Cancer Res 1992; 52:5656–5662.

32. Irimura T, Nakajima M, Nicolson G L: Chemically modified heparins as inhibitors of heparan sulfate specific endo-b-glucuronidase (heparanase) of metastatic melanoma cells. Biochemistry 1986; 25:5322–532.

33. Coombe D R, Parish C R, Ramshaw I A, Snowden J M: Analysis of the inhibition of tumor metastasis by sulfated polysaccharides. Int J Cancer 1987; 39:82–8

34. Ornitz D M, Yayon A, Flanagan J G, Svahn C M, Levi E, Leder P: heparin is required for cell-free binding of βFGF to a soluble receptor and for mitogenesis in whole cells. Mol Cell Biol 1992; 12:240–247.

35. Yayon A, Klagsbrun M, Esko J D, Leder P, Omitz D M: Cell surface, heparin-like molecules are required for binding of basic fibroblast growth factor to its high affinity receptor. Cell 1991; 64:841–848.

36. Aviezer D, Levi E, Safran M, Svahn C-M, Buddecke E, Schmidt A, David G, Vlodavsky I, Yayon A: Differential structural requirements of heparin and heparan sulfate proteoglycans that promote basic fibroblast growth factor receptor binding. J Biol Chem. 1994; 269:114–121.

37. Bartlett M. R., Underwood P. A, Parish C. R.: Comparative analysis of the ability of leukocytes, endothelial cells and platelets to degrade the subendothelial basement membrane: evidence for cytokine dependence and detection of a novel sulfatase. Immonol. Cell Biol. 1995; 73: 113–124.

38. Nakajima M., Irimura T., Nicolson G. L: A solid phase substrate of heparanase: its application to assay of human melanoma for heparan sulfate degradative activity. Anal. Biochem. 1986; 157: 162–171.

39. Oosta G. M., Favreau L. V., Beeler D. L. Rosenberg R. D: 1982. J. Biol. Chem. 257, 11249–11255.

40. Sewell R F, Brenchley P E G, Mallick N P: Human mononuclear cells contain an endoglycosidase specific for heparan sulfate glycosaminoglycan demonstrated with the use of a specific solid-phase metabolically radiolabelled substrate. Biochem. J. 1989; 264: 777–783.

41. Freeman C, Parish C R: A rapid and quantitative assay for the detection of mammalian heparanase catalitic activity. Biochem J. 1997; 325: 229–237.

42. Mullings R, Parish J H: New reducing sugar assay for the study of cellulases. Enzyme Microb. Technol. 1984; 6: 491–496.

43. Taylor K A, Buchanan-Smith J G: A colorimetric method for the quantitation of uronic acids and specific for galacturonic acid. Anal. Biochem. 1992; 201:190–196.

44. Linhardt R J: Capillary electrophoresis of oligosaccharides. In: Methods in Enz. 1994 Vol. 230. Guide to techniques in glycobiology (WJ Lennarz, GW Hart eds.): 265–280.

45. Basu S S, Dastgheib-Hosseini S, Hoover G, Li Z, Basu s: Analysis of glycosphingolipids by fluorophore-assisted carbohydrate electrophoresis using ceramide glycanase from *Mercenaria mercenaria*. Anal. Biochem. 1994; 222: 270–274.

46. Jackson P. The use of polyacrylamide-gel electrophoresis for high-resolution separation of reducing saccharides labeled with the fluorophore 8-aminononaphthalene-1,3,6 -trisulphonic acid. Biochem. J. 1990; 270: 705–713.

47. Coquet A, Veuthey J L, Haerdi W, Degli Agosti R: Application of a post-column fluorigenic reaction in liquid chromatography for the determination of glucose and fructose in biological matrices. Anal. Chim. Acta; 1991; 252: 173–179.

48. De Vouge M. W., Yamazaki A., Bennett S. A. L., Chen J., Shwed, P. S., Couture, C., and Bimboim, H.: Immunoselection of GRP94/Endoplasmin from a KNRK cell specific λgt11 library using antibodies directed against a putative Heparanase amino-terminal peptide. Int. J. Cancer: 1994; 56, 286–294.

49. Nadkarni, V. D. and Linhardt, R. J., Directional immobilization of heparin onto the nonporous surface of polystyrene microplates. BioTechniques .1997; 23: 382–385.

50. Bellott E. M., Bondaryk R. and Luther A. L. Closing the loop in combinatorial chemistry. European Pharmaceutical Contractor: Aug. 1–6, 1997.

51. Farndale R. W., Sayers C. A., Barrett A. J. A Direct spectrophotometric microassay for sulfated glycosaminoglycans in cartilage cultures. Connective Tissue Res. 1990; 24: 267–275.

6. The method of claim 1, wherein the agent is an anti-heparanase antibody.

7. The method of claim 1, wherein the agent is a naturally occurring agent.

8. The method of claim 1, wherein the agent is a synthetic agent.

9. The method of claim 8, wherein said synthetic agent is one of a plurality of agents belonging to a combinatorial library of similar agents.

10. The method of claim 1, wherein evaluating said effect of the agent on the catalytic activity of said heparanase enzyme toward said heparanase substrate is effected by a size separation away adapted for detection of degradation products of said heparin substrate.

11. The method of claim 10, wherein said size separation assay is selected from the group consisting of gel electrophoresis and column chromatography.

12. The method of claim 1, wherein evaluating said effect of the agent on the catalytic activity of said heparanase

What is claimed is:

1. A method of testing an agent for its potential at inhibiting heparanase catalytic activity, the method comprising the steps of interacting a heparanase enzyme with a heparin substrate in a presence and in an absence of the agent and determining an inhibition effect of the agent on the catalytic activity of said heparanase enzyme toward said heparin substrate.

2. The method of claim 1, wherein said heparanase is of a human origin.

3. The method of claim 1, wherein said heparanase enzyme is recombinantly expressed in an expression system selected from the group consisting of an insect cell expression system, a mammalian cell expression system and a yeast cell expression system.

4. The method of claim 1, wherein said heparin substrate is selected from the group consisting of free-heparin and immobilized heparin.

5. The method of claim 4, wherein said immobilized heparin is heparin-sepharose.

enzyme toward said hepartanase substrate is effected by a colorimetric assay.

13. The method of claim 12, wherein said colorimetric assay is selected from the group consisting of a carbazole assay, a methylene blue assay and a tetrazulium assay.

14. A method of screening for agents inhibiting heparanase catalytic activity and hence potentially inhibiting tumor metastasis, autoimmunity and inflammatory diseases, the method comprising the steps of interacting a heparanase enzyme with a heparin substrate in a presence and in an absence of the agent and determining an inhibition effect the agent on the catalytic activity of said heparanase enzyme toward said heparin substrate.

15. The method of claim 14, wherein said heparanase is of a human origin.

16. The method of claim 14, wherein said heparanase enzyme is recombinantly expressed in an expression system selected from the group consisting of an insect cell expression system, a mammalian cell expression system and a yeast cell expression system.

17. The method of claim 14, wherein said heparin substrate is selected from The group consisting of free-heparin and immobilized heparin.

18. The method of claim 14, wherein the agent is an anti-heparanase antibody.

19. The method of claim 14, wherein the agent is a naturally occurring agent.

20. The method of claim 14, wherein the agent is a synthetic agent.

21. The method of claim 20, wherein said synthetic agent is one of a plurality of agents belonging to a combinatorial library of similar agents.

22. The method of claim 14, wherein evaluating said effect of the agent on the catalytic activity of said heparanase enzyme toward said heparanase substrate is effected by a size separation assay adapted for detection of degradation products of said heparin substrate.

23. The method of claim 22, wherein said size separation assay is selected from the group consisting of gel electrophoresis and column chromatography.

24. The method of claim 14, wherein evaluating said effect of the agent on the catalytic activity of said heparanase enzyme toward said heparanase substrate is effected by a colorimetric assay.

25. The method of claim 24, wherein said colorimetric assay is selected from the group consisting of a carbazole assay, a methylene blur assay and a telrazulium assay.

26. A quantitative method of testing an agent for its potential at inhibiting heparanase catalytic activity, the method comprising the steps of interacting a heparanase enzyme with a heparanase substrate in a presence and in an absence of the agent and determining, in solution, a number of cleavages of said heparanase substrate in said presence as being compared to said absence of the agent by an assay adapted for detection of reducing moieties associated with degradation products of said heparanase substrate, thereby quantitatively determining the potential of the agent at inhibiting the heparanase catalytic activity in solution, without a need for a size separation step.

27. The quantitative method of claim 26, wherein said heparanase is a natural heparanase.

28. The quantitative method of claim 26, wherein said heparanase is a recombinantly produced heparanase.

29. The quantitative method of claim 28, wherein said recombinantly produced heparanase is of a human origin.

30. The quantitative method of claim 28, wherein said recombinantly produced heparanase is expressed in an expression system selected from the group consisting of an insect cell expression system, a mammalian cell expression system and a yeast cell expression system.

31. The quantitative method of claim 26, wherein said heparanase substrate is an extracellular matrix or a portion thereof.

32. The quantitative method of claim 31, wherein said heparanase substrate includes macromolecules associated with said extracellular matrix.

33. The quantitative method of claim 32, wherein said macromolecules include heparan sulfate proteoglycans.

34. The quantitiative method of claim 26, wherein said heparanase substrate includes extracellular matrix-derived soluble heparan sulfate proteoglycans.

35. The quantitative method of claim 26, wherein said heparanase substrate is selected from the group consisting of heparan sulfate, heparin, heparin-sepharose, and derivatives thereof.

36. The quantitative method of claim 26, wherein said heparanase substrate is selected from the group consisting of heparin and immobilized heparin.

37. The quantitative method of claim 26, wherein said heparanase substrate is immobilized.

38. The quantitative method of claim 26, wherein the agent is an anti-heparanase antibody.

39. The quantitative method of claim 26, wherein the agent is a naturally occurring agent.

40. The quantitative method of claim 26, wherein the agent is a synthetic agent.

41. The quantitative method of claim 40, wherein said synthetic agent is one of a plurality of agents belonging to a combinatorial library of similar agents.

42. The quantitative method of claim 26, wherein said assay is a colorimetric assay.

43. The quantitative method of claim 4, wherein said colorimetric assay is a tetrazolium blue assay in which tetrazolium blue is reduced to a soluble colored formazan salt.

44. A quantitative method of screening for agents inhibiting heparanase catalytic activity and hence potentially inhibiting tumor metastasis, autoimmunity and inflammatory diseases, the method comprising the steps of interacting a heparanase enzyme with a heparanase substrate in a presence and in an absence of the agent and determining, in solution, a number of cleavages of said heparanase substrate in said presence as being compared to said absence of the agent by an assay adapted for detection of reducing moieties associated with degradation products of said heparanase substrate, thereby quantitatively determining the potential of the agent at inhibiting the heparanase catalytic activity in solution, without a need for a size separation step.

45. The quantitative method of claim 44, wherein said heparanase is a natural heparanase.

46. The quantitative method of claim 44, wherein said heparanase is a recombinantly produced heparanase.

47. The quantitative method of claim 46, wherein said recombinantly produced herparanase is of a human origin.

48. The quantitative method of claim 46, wherein said recombinantly produced heparanase is expressed, in an expression system selected from the group consisting of an insect cell expression system, a mammalian cell expression system and a yeast cell expression system.

49. The quantitative method of claim 44, wherein said heparanase substrate is an extracellular matrix or a portion thereof.

50. The quantitative method of claim 49, wherein said heparanase substrate includes macromolecules associated with said extracellular matrix.

51. The quantitative method of claim 50, wherein said macromolecules include heparan sulfate proteoglycans.

52. The quantitative method of claim 44, wherein said heparanase substrate includes extracellular matrix-derived soluble heparan sulfate proteoglycans.

53. The quantitative method of claim 44, wherein said heparanase substrate is selected from the group consisting of heparan sulfate, heparin, heparin-sepharose, and derivatives thereof.

54. The quantitative method of claim 44, wherein said heparanase substrate is selected from the group consisting of heparin and immobilized heparin.

55. The quantitative method of claim 44, wherein said heparanase substrate is immobilized.

56. The quantitative method of claim 44, wherein the agent is an anti-heparanase antibody.

57. The quantitative method of claim 44, wherein the agent is a naturally occurring agent.

58. The quantitative method of claim 44, wherein the agent is a synthetic agent.

59. The quantitative method of claim 58, wherein said synthetic agent is one of a plurality of agents belonging to a combinatorial library of similar agents.

60. The quantitative method of claim 44, wherein said assay is a colorimetric assay.

61. The quantitative method of claim 60, wherein said colorimetric assay is a tetrazolium blue assay in which tetrazolium blue is reduced to a soluble colored formazan salt.

* * * * *

UNITED STATES PATENT AND TRADEMARK OFFICE
CERTIFICATE OF CORRECTION

PATENT NO. : 6,190,875 B1
DATED : February 20, 2001
INVENTOR(S) : Ben-Artzi et al Page 1 of 1

It is certified that error appears in the above-identified patent and that said Letters Patent is hereby corrected as shown below:

Title page,
Item [75], Inventors, "Hanna Ben-Artzi, Zion; Maty Ayal-Hershkovitz, Herzliya; Israel Vlodavsky; Iris Pecker, both of Zion; Yoav Peleg; Daphna Miron, both of Rehovot, all of (IL)"
should read -- Hanna Ben-Artzi, Rishon Le-Zion; Maty Ayal-Hershkovitz, Herzliya; Israel Vlodavsky; Iris Pecker, both of Rishon Le-Zion; Yoav Peleg; Daphna Miron, both of Rehovot, all of (IL) --

Column 30,
Line 12, "away" should read -- assay --.
Line 50, "hepartanase" should read -- heparanase --.

Column 31,
Line 26, "blur" should read -- blue --.
Line 26, "telrazulium" should read -- tetrazolium --.

Column 32,
Line 14, "4" should read -- 42 --.

Signed and Sealed this

Nineteenth Day of March, 2002

Attest:

JAMES E. ROGAN
*Director of the United States Patent and Trademark Office*

*Attesting Officer*